US008101551B2

(12) United States Patent  
Stewart et al.

(10) Patent No.: US 8,101,551 B2  
(45) Date of Patent: Jan. 24, 2012

(54) PRODUCTION AND USE OF ENDOPHYTES AS NOVEL INOCULANTS FOR PROMOTING ENHANCED PLANT VIGOR, HEALTH, GROWTH, YIELD REDUCING ENVIRONMENTAL STRESS AND FOR REDUCING DEPENDENCY ON CHEMICAL PESTICIDES FOR PEST CONTROL

(75) Inventors: James F. Stewart, Kitchener (CA); William G. Brown, Kingsville (CA)

(73) Assignee: Adjuvants Plus Inc., Kingsville, Ontario (CA)

( * ) Notice: Subject to any disclaimer, the term of this patent is extended or adjusted under 35 U.S.C. 154(b) by 786 days.

(21) Appl. No.: 12/293,923

(22) PCT Filed: Mar. 22, 2007

(86) PCT No.: PCT/CA2007/000455  
§ 371 (c)(1),  
(2), (4) Date: Sep. 22, 2008

(87) PCT Pub. No.: WO2007/107000  
PCT Pub. Date: Sep. 27, 2007

(65) Prior Publication Data  
US 2009/0105076 A1 Apr. 23, 2009

Related U.S. Application Data

(60) Provisional application No. 60/784,480, filed on Mar. 22, 2006.

(51) Int. Cl.  
C05F 11/08 (2006.01)  
A01N 63/04 (2006.01)  
A01P 3/00 (2006.01)  
A01P 7/00 (2006.01)  
A01P 21/00 (2006.01)  
C12P 1/02 (2006.01)

(52) U.S. Cl. ........... 504/117; 504/100; 504/116.1; 424/93.5

(58) Field of Classification Search .............. None  
See application file for complete search history.

(56) References Cited

FOREIGN PATENT DOCUMENTS  
CA 2178601 7/1995

OTHER PUBLICATIONS

Morandi, M.A.B. et al., "Relationships of Aphid and Mite Infestations to Control of *Botrytis cinerea* by *Clonostachys rosea* in Rose (*Rosa hybrida*) Leaves", Phytoparasitica, Mar. 2000, vol. 28 (1), pp. 1-9.

(Continued)

*Primary Examiner* — Johann Richter  
*Assistant Examiner* — Erin Hirt  
(74) *Attorney, Agent, or Firm* — David L. Conn; Borden Ladner Gervais LLP

(57) ABSTRACT

A process and method for the production of endophytes as plant inoculant products, specifically *Clonostachys rosea* strain 88-710, for the promotion of plant vigor, health, growth and yield are disclosed. The endophyte, *Clonostachys rosea* strain 88-710 produces a fungal conidial preparation by utilizing a discrete solid substrate fermentation system, namely Potato Dextrose Agar or Malt Extract Agar. Additionally, the endophyte, *Clonostachys rosea* strain 88-710, can act as an inoculant to stimulate and have an additive effect with *rhizobium* bacteria on the production of nitrogen fixing nodules on legumes and growth enhancement e.g. beans, soybeans, peas and alfalfa. As well, *Clonostachys rosea* strain 88-710, can combine with rooting hormones, e.g. indole-3-butyric acid (IBA) to provide inoculant and rooting benefits to cuttings/transplants of plants.

15 Claims, 11 Drawing Sheets

OTHER PUBLICATIONS

Sutton, J.C. et al., "Ability of *Clonostachys rosea* to Establish and Supress Sporulation Potential of *Botrytis cinera* in Deleafed Stems of Hydroponic Greenhouse Tomatoes" Biocontrol Science and Technology,Mar. 2002, 12, pp. 413-425.

Shafia, A. et al., "Influence of preinoculation light intensity on development and interactions of *Botrytis cinerea* and *Clonostachys rosea* in tomato leaves", Can. J. Plant Pathol.,Sep. 2001, 23, pp. 346-357.

Morandi, M. A. B. et al., "Development of *Clonostachys rosea* and Interactions with *Botrytis cinerea* in Rose Leaves and Residues", Phytoparasitica,Jan. 2001, 29(2), pp. 103-113.

PCT Application No. CA2007/000455: International Search Report dated Jul. 5, 2007.

Morandi, M.A.B. et al., "Effects of Host and Microbial Factors on Development of *Clonostachys rosea* and control of *Botrytis cinera* in rose", European J. Plant Pathol.,Feb. 2000, 106, pp. 349-448.

Morandi, M.A.B. et al., "Suppression of *Botrytis cinerea* sporulation by *Clonostachys rosea* on rose debris: a valuable component in *Botrytis blight* management in commercial greenhouses", Biological control,Mar. 2003, 26, pp. 311-317.

Yohalem, D.S et al., "Biocontrol agents efficiently inhibit sporulation of *Botrytis aclada* on necrotic leaf tips but spread to adjacent living tissue is not prevented", FEMS Microbiology Ecology,Jan. 2004, 47, pp. 297-303.

Yohalem, D.S, "Evaluation of fungal antagonists for grey mould management in early growth of pot roses", Ann. Appl. Biol., Feb. 2004, 144, pp. 9-15.

Moller, K. et al., "Biocontrol of *Pythium tracheiphilum* in Chinese Cabbage by *Clonostachys rosea* under Field Conditions", Biocontrol Science and Techn., Apr. 2003, 13, pp. 171-182.

Schroers, H-J et al., "Classification of the mycoparasite *Gliocladium roseum* in *Clonostachys* as *C. rosea*, its relationship to *Bionectria ochroleuca*, and notes on other *Gliocladium*-like fungi", Mycologia, Mar. 1999, 91(2), pp. 365-385.

"Development of Endophyte Technologies to Promote Vigor, Fitness and Productivity of Miniature Roses" , Final Report on a research project for Adjuvants Plus. Inc., Kingsville, Ontario. Sep. 30, 2002 [retrieved on May 17, 2007]. Retrieved from the internet: <URL: http://www.endofine.net/docs/EndofineTrial.pdf>.

** Sporulation of *Botrytis* on the senescent / dead tissues (0 – 100 scales)

Effects of *Clonostachys rosea* (Cr) and *Pseudomonas chlororaphis* (Psc), applied separately and in combination to the nutrient solution, on leaf area of hydroponic cucumber at 16 and 19 days after treatment.

Effects of *Clonostachys rosea* (Cr) and *Pseudomonas chlororaphis* (Psc), applied separately and in combination to the nutrient solution, on dry mass of the roots, shoots, and whole plants of hydroponic cucumbers at 19 days after treatment.

Fig 9 Colonisation of rose plant shoots and roots using EndoFine alone and in combination with IBA rooting compound.
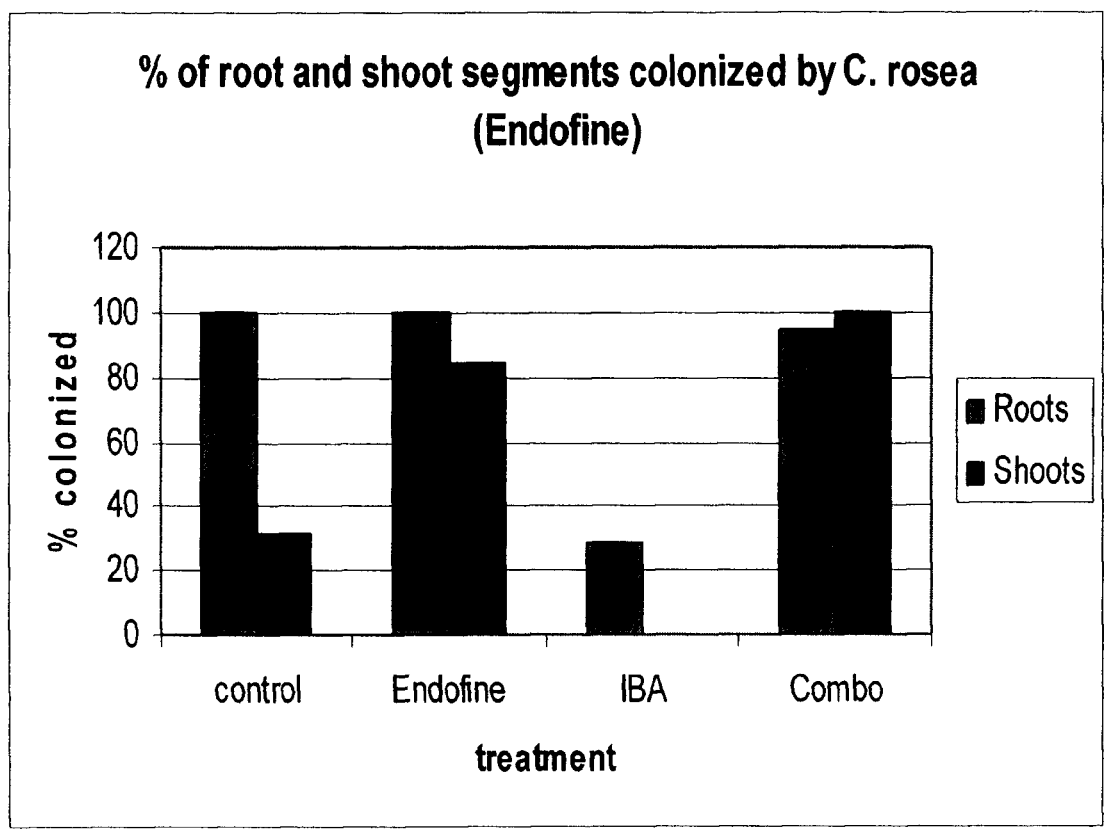

Fig 10 Root weight Gains of rose plant roots and roots using EndoFine alone and in combination with IBA rooting compound.
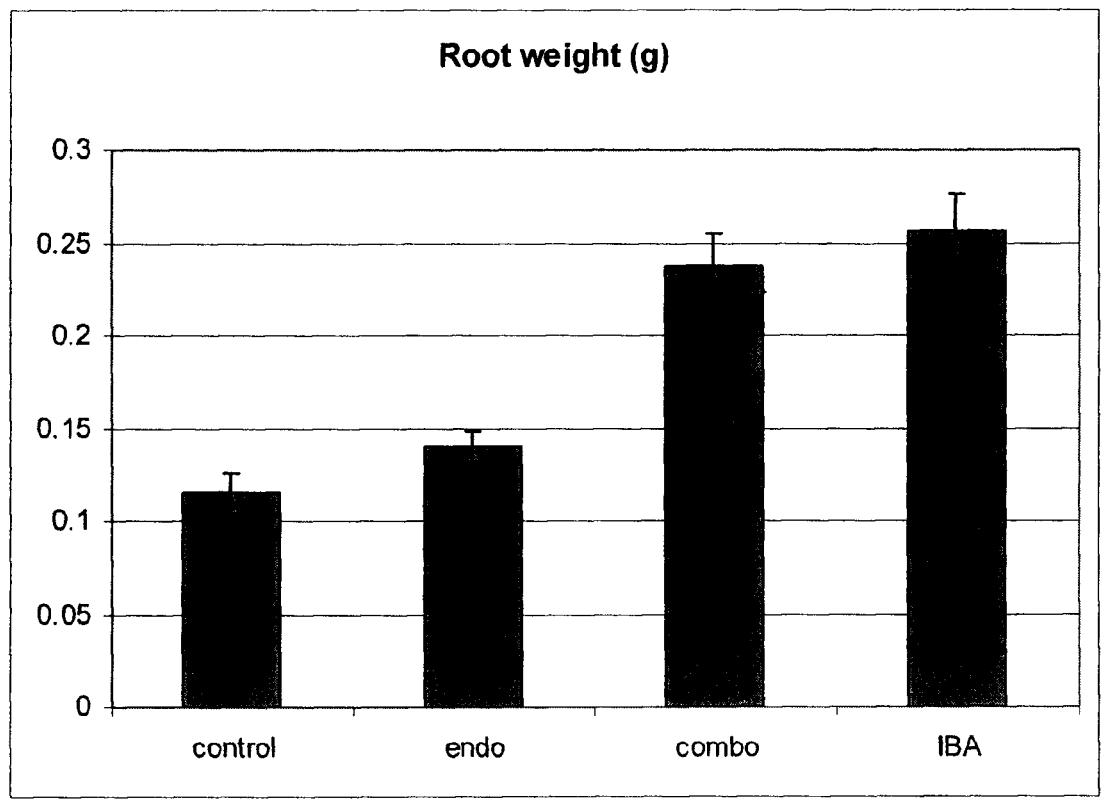

PRODUCTION AND USE OF ENDOPHYTES AS NOVEL INOCULANTS FOR PROMOTING ENHANCED PLANT VIGOR, HEALTH, GROWTH, YIELD REDUCING ENVIRONMENTAL STRESS AND FOR REDUCING DEPENDENCY ON CHEMICAL PESTICIDES FOR PEST CONTROL

FIELD OF INVENTION

The present invention relates to a production and use process whereby endophytes are identified as inoculant products, specifically the fungus *Clonostachys rosea* strain 88-710, provides for:
(1) Unique inoculant feature/benefits for the promotion of plant vigor, health, growth and yield.
(2) A process for making the product(s) that provides for various levels of highly viable/stable spores and mycelia material in stable formulations that prevents the degradation of a living endophyte *C. rosea*.
(3) The product formulation allows/enables practical use and application of the product(s) to seeds, roots, stems, leaves, flowers, bulbs, etc of plants as a water based sprayable formulations or as a dusts for other uses e.g. seed treatment and insect vectoring.
(4) Allows the product (as an endophyte) to be formulated into value-added products that provide unique feature/benefits to provide natural induced plant resistance to fungal diseases such as powdery mildew, *botrytis*, root rots, seed seed decay, wilt diseases and or insects/mites.
(5) and allows the product (endophyte) when applied to roots, stems, leaves, flowers, wounds or cut surfaces of plants to act as an inoculant 'enhanced site occupier' within the tissues of plants.
(6) and endophyte product provides improved root, leaf, stem and or vegetative bud (flowers) growth to plants as well as seed germination and
(7) for reduction of environmental or cultural stress by providing induced natural plant resistance to plants e.g. root stresses due to trimming, pruning, cutting, wounding or other stresses with the net result of:
(8) Improved crop quality and faster development to marketability of the crop.
(9) A strain of *Clonostachys rosea* i.e. 88-710 with a unique genetic coding that differentiates the endophyte reproductively from other fungal strains of *Clonostachyus rosea* or *Gliocladium roseum*.
(10) An endophyte *Clonostachys rosea* strain 88-710 acts as an inoculant to stimulate and have an additive effect with soil *rhizobium* bacteria for the production of nitrogen fixing nodules on legumes for growth enhancement e.g. soybeans.

DEFINITIONS

The term endophyte as described in this invention is defined as (1) a "site occupier" i.e. endophytes "or fungi or bacteria that form symptom-less infections, for part or all of their life cycle within healthy leaves and stems of plants" (Definition by Hawksworth et al, 1995). (2) a microbe living symbiotically or commensally in a host plant.

The term inoculant as described in this invention is defined in several Federal, or State regulations as (1) "substances other than fertilizers, manufactured, sold or represented for use in the improvement of the physical condition of the soil or to aid plant growth or crop yields" (Canada Fertilizers Act) or (2) "a formulation containing pure or predetermined mixtures of living bacteria, fungi or virus particles for the treatment of seed, seedlings or other plant propagation material for the purpose of enhancing the growth capabilities or disease resistance or otherwise altering the properties of the eventual plants or crop" (Ad hoc European Working Group, 1997) or (3) Soil or plant inoculants shall include any carrier or culture of a specific micro-organism or mixture of micro-organisms represented to improve the soil or the growth, quality, or yield of plants, and shall also include any seed or fertilizer represented to be inoculated with such a culture (New York State 10-A Consolidated Law) or (4) "meaning any chemical or biological substance of mixture of substances or device distributed in this state to be applied to soil, plants or seeds for soil corrective purposes; or which is intended to improve germination, growth, quality, yield, product quality, reproduction, flavor, or other desirable characteristics of plants or which is intended to produce any chemical, biochemical, biological or physical change in soil (Section 14513 of the California Food and Agriculture Code).

The term mycoparasite as described in this invention is defined as (1) A fungus that parasitizes anther fungus (2) a fungal parasitism of another fungus or fungi (3) an organism which attacks and feeds on fungi.

The term hyperparasite as described in this invention is defined as an organism that is parasitic on other parasites.

*Clonostachys rosea* strain 88-710 defined as the specific endophyte fungus isolated and screened from field samples in Ontario and produced under the novel production technique described in this invention.

The term EndoFine® is defined as the product formulation/brand name for product formulations of *Clonostachyus rosea* strain 88-710 and is a registered trademark of Adjuvants Plus Inc.

ADJ 702 is defined as the product code for a specific formulation of *Clonostachys rosea* strain 88-710 containing natural components in the form of calcium, carbonate, potassium salts, and natural emulsifiers (food grade proteins, lactose) that provides rapid wound healing and site occupation benefits as an inoculant that in turn, also provides additional plant inoculant protective benefits against a wide range of plant diseases, insects and mites e.g. powdery mildew, two-spotted mites, aphids.

The term *Bionectria ochroleuca* is referred to as the reference *Mycologia*: Vol. 91, No. 2, pp. 365-385.1999. Classification of the mycoparasite *Gliocladium roseum* in *Clonostachys* as *C. rosea*, its relationship to *Bionectria ochroleuca*, and notes on other *Gliocladium*-like fungi. Hans-Josef Schroers, Gary J. Samuels, Keith A. Seifert, and Walter Gams

BACKGROUND OF THE INVENTION

Endophytes such as the fungus *Clonostachys rosea* formerly called *Gliocladium roseum*, have been most commonly described in the literature as a "site occupier" i.e. endophytes "or fungi or bacteria that form symptom less infections, for part or all of their life cycle within healthy leaves and stems of plants" (Definition by Hawksworth et al, 1995).

Sample data on endophytes such as the fungus *Clonostachys rosea* or *Gliocladium roseum* (as it was formerly known), indicate that the fungus occurs worldwide in a variety of soils e.g. Europe, North America, Latin America, etc. However not all strains of *Clonostachys rosea* are the same in morphology, reproductively or have the same genetic material. Strain 88-710 described in this invention is unique reproductively to the fungus species *Clonostachyus*.

The background for the classification of *Clonostachys rosea* is described in the reference i.e. (*Mycologia*: Vol. 91, No. 2, pp. 365-385.1999. Hans-Josef Schroers, Gary J. Samuels, Keith A. Seifert, and Walter Gams.

Because the common soil fungus and mycoparasite *Gliocladium roseum* differs from the type species of *Gliocladium*, *G. penicillioides*, in morphology, ecology, teleomorph, and DNA sequence data, it is classified in a separate genus, *Clonostachys*. *Penicillium roseum* is the oldest available name for *G. roseum* and is recombined as *C. rosea*. *Penicillium roseum*, described from potato in Germany, is neotypified by a conidial isolate originating from a fungal substratum in European soil. By choosing this strain as neotype for *P. roseum* the epithet is formally linked to the common soil fungus used in the biocontrol of fungal plant pathogens. The anamorph of *Bionectria ochroleuca* (Hypocreales) is morphologically indistinguishable from *C. rosea*; both morphs are redescribed. Bionectria is generically distinct from *Nectria* s. s. and is the appropriate genus for species of the *Nectria ochroleuca* group. The anamorph genus *Gliocladium* s. s. is associated with teleomorphs in *Sphaerostilbella* and *Hypocrea* series *Pallidae*. With the separation of Clonostachys from *Gliocladium* and Bionectria from *Nectria* the generic classification reflects natural relationships. A generic circumscription is proposed for *Clonostachys* and compared with *Gliocladium*. *Nectriopsis sporangiicola* and *Roumegueriella rufula* are related to Bionectria but have distinct *Gliocladium*-like anamorphs. Based on morphological features, *Rhopalocladium myxophilum* gen. et sp. nov. is proposed for the anamorph of *N. sporangiicola*. The anamorph of *Roumegueriella rufula* is generally found in association with the teleomorph and is referred to as *Gliocladium*-like.

Not all endophytes respond to plants in the same way. Endophytes are known to infect healthy plants e.g. via wounds e.g. mechanical damage caused by insects or diseases and in some instances research has documented certain endophytes to provide some measure of plant disease or control of insect pests.

However, little or no documentation has been provided that show endophytes to act as inoculants to promote plant health, growth or vigor and capable of providing "natural inoculant induced plant resistance (IIR)" to environmental stresses. Moreover, little or no information has been provided to show that specific endophytes such as the strain 88-710 of *Clonostachys rosea* when acting as an inoculant can also co-exist with other beneficial fungi, bacteria or viruses to provide additive or stimulated growth benefits.

For example, there is no known data or information that demonstrates that a fungus esp. an endophyte e.g. *Clonostachys rosea* strain 88-710 can act as an inoculant to stimulate the production of nitrogen fixing nodules on legumes e.g. soybeans. Until this invention, it was thought that only naturally occurring bacteria e.g. *Rhizobium* were capable of producing and stimulating the production of nitrogen fixing nodules on legume plants and reducing dependency on chemical fertilizers. This invention teaches that *Clonostachyus rosea* strain 88-710 can act as an inoculant to stimulate and be additive (beneficially interactive with nitrogen fixing bacteria) in the production of nitrogen fixing nodules on legumes e.g. soybeans This invention describes new examples/traits about endophytes such as the strain 88-710 of *Clonostachys rosea* that are novel, inventive, useful that teaches something new. The fungus called *Clonostachys rosea* (*C. rosea*) although it occurs in virtually all parts of the world, in various strains/ forms and in various climate zones, it has most often been characterized as a closely (morphological) counterpart of *Penicillium* with slimy/sticky conidia. The role and function of *Penicillium* spp. as inoculants, is well documented but the inoculant function and mode of action of its closely related relative i.e. the endophyte *C. rosea* has not been documented, quantified or demonstrated until this invention.

Until recently, the role or mode of action of endophytes such as *C. rosea* was not fully understood and it was thought that all strains of *C. rosea* exhibited only biocontrol modes of action; most such studies were conducted in the presence of plant diseases and not in the absence or near absence of plant diseases. The data appeared to only measure or indicate that *C. rosea* or *Glioclaidium roseum* (as it was previously known) may control various fungal infections of plants as a biocontrol agent e.g. mycoparasite or hyperparasite by exuding antibiotics, metabolites or mycoparasitic enzymes.

However, as this invention shows, endophytes such as *C. rosea*, strain 88-710 do not directly control fungal or bacterial diseases nor do they have a direct mitigating role of controlling plant pests i.e. diseases or insects, mites, etc. by exuding antibiotics, toxic metabolites or enzymes. Rather as the novelty of this invention will demonstrate, is that *C. rosea* acts as a true inoculant on plant tissues to promote plant health, size, root growth or increases yield and also can aid in reducing or eliminating the use of chemical fungicides while as it imparts natural induced plant resistance with suitable formulations to environmental stresses such as plant diseases, moisture reduction, insects and mites. It does this mainly by having the ability to rapidly colonise plant tissue (living or senescing tissue), imparting resistance to the plant while occupying the tissue thus denying such tissue to infection by disease organisms, and other stresses while assisting the plant to uptake nutrients.

The current invention also describes *C. rosea* strain 88-710 as providing plant health benefits to plants irrespective of whether a pathogen is present, hence true non-biocontrol features.

The mode of action of *C. rosea* strain 88-710 thus appears instead to be one of it ability to provide a rapid first presence as an "inoculant site occupier" to leaves, stems, and roots thereby promoting plant vigor, plant health, growth and stress reduction such as the prevention of root biomass loss during stem trimming. This ability to help plants retain good root mass/growth helps plants ward off or re-cover from the shock of trimming (bonsai effect) resulting in faster re-generation of stem growth and better utilization of nutrients. It also acts in the same way to overcome other stresses to plants whether those stresses are environmental or cultural.

Moreover, endophytes such as *C. rosea*, strain 88-710 are thought to work by enhancing the solubility/availability of plant nutrients e.g. phosphorus (Reference: Tilak, K. V. B. R et al "Diversity of Plant Growth and Soil Health Supporting Bacteria", July 2005 Current Science Vol 89 N01). This novel invention will show that the strain 88-710 of *Clonostachyus rosea* acts to enhance nitrogen, phosphorus, and potassium uptake as well micronutrients in plants and can act complementary/additive to nitrogen fixing *Rhizobium* bacteria. Moreover, this invention demonstrates that endophytes such as *C. rosea* can be combined with other beneficial bacteria, or fungi due to the fact that the 88-710 strain of *C. rosea* is not toxic to such organisms i.e. does not exude toxic metabolites, antibiotics or enzymes as to other bio-control fungi or mycoparasites. One of the key feature benefits of inoculants is that true inoculants can be ad-mixed together for mutual benefit, unlike bio-control agents.

This invention will show that some endophytes such as *C. rosea* strain 88-710, are more specialized in that they possess the ability to penetrate inside root tissues, leaves, stems, etc of plants and have direct access to organic compounds present in the apoplast". Once inside the apoplast of plant tissues, endophytes such as *C. rosea* can survive and exude volatile exudates/compounds that promote plant health as well induce the plant to protect itself from various stress factors via IIR (inoculant induced resistance) e.g. as disease infections (*botrytis, fusarium, Pythium*, etc.) and or insect/mite attack. *C. rosea* has the unique inoculant feature/benefit of living within living and or senescent plant tissue and either remaining dormant or using that tissue as food to provide plants with nutrition even though the plant tissue may have been wounded by a disease, mite or insect. All of these are hitherto new, inventive, novel and useful features for endophytes acting as inoculants.

As indicated, Endophytes may also promote growth directly by the fixation of nitrogen alone or in combination with nitrogen fixing bacteria and or solubilization of minerals such as phosphorus, and provide the production of non-toxic siderophores that solubilize or sequester iron and other key micronutrients (manganese, zinc, etc.). The above inventive, novelty, application and new teachings of this invention show the endophyte inoculant benefits of promoting plant vigor, health and growth. In order for endophytes e.g. *C. rosea*, strain 88-710 to exhibit such benefits, the endophyte e.g. *C. rosea* needs to be present in sufficient quality/quantity and in a useful bio-available emulsifiable form as an effective and rapid 'site occupier' i.e. stable, robust spores in a deliverable formulation. The claims of this invention provide those rapid "site occupier" characteristics.

This invention also describes a novel, inventive and use application (improved sporulation and stability), for the production of an endophyte e.g. *C. rosea* that optimizes manufacture, concentration and thereby the performance of an endophyte product, for various uses as an inoculant(s).

Moreover naturally occurring endophytes such as *C. rosea*, strain 88-710 (which was originally identified from some 1400 different naturally occurring field isolates (samples) from Ontario strawberry fields, would have remained a relatively ineffective obscure endophyte/inoculant was rendered effective by this invention to provide the above inoculant plant health benefits and induced plant disease/insect/mite reduction feature/benefits by being available in a practical, useful and effective (as a site occupier) product formulations against major plant pathogens/insect pests e.g. *Botrytis cinerea* (grey mould). Without these key production and physical traits, endophytes such as *C. rosea* might remain relatively ineffective as inoculants.

This invention is also particularly applicable where wounding during pruning, cuttings, wounding, root trimming, transplanting/transplants and the like occurs.

The use of endophytes as inoculants, such as *C. rosea*, has the potential to offer a number of feature/benefits to help counter inadequacies, periodic failures and concerns associated with present pest control and costly agronomic cultural practices. These include cultural and sanitation measures, regulation of the microclimate, and reduce the heavy dependency on synthetic fungicides/insecticides with consequences such as fungicidal/insecticidal resistance, environmental and human exposure/loading and the general reduction of production costs, the reduction of energy needs/costs (hence reduction of greenhouse gases/contaminants), time to market, and enhancement of crop quality.

A patent has been granted e.g. U.S. Pat. No. 6,495,133 Dec. 17, 2002 using a certain strain coded ATCC # 74447 of *Gliocladium roseum* as a biocontrol agent for controlling diseases caused by fungal pathogens e.g. *Fusarium, Ascochyta, Pythium, Rhizoctonia* in plants for treatment of seeds, soil or plants (pea, bean, canola, wheat, barley, horticultural and ornamental plants). Patents have also been granted e.g. U.S. Pat. No. 6,475,566 Nov. 5, 2002 or U.S. Pat. No. 5,344, 252 Jul. 9, 1996 for the protection of lumber against sapstains or fungi. However, none of these patents identified the novel usefulness of this invention for *Clonostachys rosea*, strain 88-710 or endophytes as beneficial inoculants for promoting plant vigor, health and growth in plants in the absence of disease or insect pressures or this combined with induced plant resistance to environmental stresses by plants themselves.

In particular, outlined in this invention, the need to identify and provide the correct physical properties to an endophyte for a high level of inoculant "rapid site occupation" to ensure performance in plants that in turn provides for improved leaf, stem and root growth and thereby reducing stress factors (environmental as well as cultural) of plants.

There have also been examples of other patents granted for endophytes e.g. U.S. Pat. No. 6,815,591 Nov. 9, 2004, or U.S. Pat. No. 5,723,720 Mar. 3, 1998, that provide plants via seed with imported insect resistance and drought tolerant traits into plants. However, again these patents do not document inventiveness, novelty, or usefulness regarding enhanced plant growth, overall plant health enhancement or these traits combined with plant inoculant resistance to stresses e.g. diseases or the ability to enhance endophyte product formulations to provide added value inoculant feature/benefits to allow plants themselves to resist attack from pests.

Other patents e.g. U.S. Pat. No. 4,550,527 Nov. 5, 1985 describe methods using special soil mixtures and containers of how to best infect roots of plants with beneficial mycorrhizal fungi for the purposes of improving plant health but these methods are not related to endophytes or to specific endophytes such as *C. rosea* esp. strain 88-710 or to specific feature/benefits of site inoculation and growth enhancement.

The present invention overcomes drawbacks in the prior art and teaches something new for information in the public domain. The drawbacks are overcome by a combination of the features of the main claims. The sub-claims disclose further advantageous embodiments of the invention and may also overcome drawbacks in the prior art. The present invention provides for many of the key feature/benefits the marketplace is seeking e.g.:

(1) Natural Endophyte products such as *C. rosea*, strain 88-710 that can act as plant inoculants that provide unique feature/benefits for the promotion of plant vigor, health, growth and yield including stimulation of legume plants to produce nodules for fixation of nitrogen (until this invention an unknown mode of action for fungal endophytes)

(2) Natural crop enhancement products that can increase yields, quality and reduce growing periods amidst environmental and cultural stresses e.g. drought, better utilization of nutrients, thus lowering energy costs and consequences of inefficient use of energy.

(3) Little or no risk of increased environmental or contaminate hazards due to the use of conventional agrochemicals/pesticides or fertilizers.

(4) Effective production of a natural bio agent in a stable useful formulation(s) that imparts/enhances unique physical 'site inoculant occupation' within plant tissues that can be organically certified for a growing market need i.e. OMRI certification, that in turn (5) Imparts growth and plant protectant properties as a plant inoculant resistance effect against diseases, wounds or in a combined action for improved crop production that is unlikely to develop into "lack of performance resistance" as do chemicals pesticides.

(6) Provide natural wound healing benefits as an inoculant that can in turn in suitable formulations (that contain natural salts/emulsifiers) can provide plant protective benefits against a wide range of plant diseases, insects and mites e.g. powdery mildew, two-spotted mites, aphids.

There is strong market interest to have as agronomic tools bio agents that are naturally occurring for use in improving crop production and quality of life e.g. quality, yield and time to market that can qualify for organic certification e.g. OMRI.

The economic impact for the use of this invention is documented in terms of feature/benefits. Solutions to the recurring problem of plant pathogens have been explored for decades. As particular crops become more abundant, and the area of land allocated for agriculture expands, or as greenhouse needs expand, there is an inherent need to employ more efficient and effective agronomic practices, preferably those beneficials provided by Mother Nature herself and that occur naturally in our global environment.

As a result of increasing demand for crop production, farmers must often compromise their cultural practices by planting crops on sub-optimal land, or by increasing the frequency at which crops are planted in a specific location. In doing so, crop nutrients are depleted, a microbial shift occurs and specific crop pathogens, especially soil-borne or seed-borne pathogens, become more prevalent. Accordingly, it is increasingly difficult to sustain the health and productivity of crops. It has been well documented that the fungal species *C. rosea* occurs most abundantly in virgin soils, wherever such soils can still be found around the world; in depleted or overworked soils *C. rosea* and other beneficial endophytes has been gradually eroded and are nearly or completely absent from soils thus reducing soil productivity and hampering farmers from producing productive crops e.g. in some African soils. The need for improved soil conditioning and the beneficial chain effect on global economies could be massive.

California alone has a $1.2 billion a year fruit industry; the strawberry crop alone is estimated to be worth over $400 million annually but is under pressure to minimize water/energy inputs and produce more "organic" crops to minimize pesticide usage.

There is increasing pressure in Europe to use only organically approved crop production tools amidst a lack of such tools.

In the instance of field peas as one example of a field "pulse" crop in Canada, there were approximately 1,000,000 hectares/year of field pea grown in western Canada in 1999-2005, estimated at a total farm value of over $600+ million and other oil seed crops such as Canola when acreages have increased to over 15 million acres planted annually amidst growing input problems.

In recent years, the field pea, lentil and other specialty crops of western Canada have been most affected by soil-borne or seed-borne diseases, as well as the *Ascochyta* complexes of root and foliage. Known as PRRC (pea root rot complex) diseases, the soil-borne and seed-borne diseases are most commonly caused by the pathogens *Fusarium solani* f.sp. *pisi, Fusarium oxysporum* f.sp. *pisi, Mycosphaerella pinodes, Rhizoctonia solani, Sclerotina sclerotiorum, Aphanomyces euteiches, Alternaria alternata* and *Pythium* spp. The incidence of PRRC diseases varies with year and location, while its severity is largely dependent on climate, crop rotation and cultural practices. The yield losses of pea crops alone, as a result of PRRC pathogens including foliar infection by *Ascochyta* complex, are frequently devastating with a conservative 15%-20% yield reduction translating into an approximate annual loss of $80+ million in areas of western Canada.

The rose and flower industry is estimated to be worth over $5 to $6 billion dollars (US) in North America at the grower level. The industry normally requires some 11-14 weeks turnaround time from cuttings to market shipment. The ability to produce a higher quality product with a reduction in some 10-20 days to market (as the technology in this invention provides) is a significant cost benefit to the flower/horticultural industry.

Greenhouse vegetable crops e.g. tomato, cucumber, peppers, etc in Canada alone are worth an estimated $1.0 billion and employ over 19,000 people. The US industry is valued at more than 10 times that. Losses to individual greenhouses e.g. a cucumber grower in a production area of 44,500 $m^2$, crop productivity is frequently 10-15% lower in areas with diseased plants than where plants were generally healthy. This loss translates to more than $375,000 per year.

SUMMARY OF THE INVENTION

The present invention provides for a novel, inventive and applicable process and method for producing endophytes, specifically a fungus *Clonostachys rosea* as effective plant inoculants that provide for the promotion of plant vigor, health, growth and yield. Specifically the invention provides for:

(1) an effective plant inoculant of an endophyte product(s) produced comprising *Clonostachys rosea* strain 88-710 with unique inoculant feature/benefits for the promotion of improved plant vigor, health, quality, growth and yield (2) a process for making the product(s) that provides for various levels of highly viable/stable spores and mycelial material in a stable formulation with natural emulsifiers that prevents the degradation of a living endophyte *C. rosea* strain 88-710 and allows rapid site occupation on plants.

(3) product formulations that allow/enables practical use and application of the product(s) to seeds, roots, stems, leaves, flowers, bulbs, etc of plants as a water based sprayable formulations, as a dusts or spore concentrates for other uses including application equipment/devices of practical use by growers e.g. seed treatment or insect vectoring, spray or irrigation equipment, (4) and allows the product(s) (endophyte) when applied to, seeds, roots, stems, leaves, flowers, wounds or cut surfaces of plants to act as an inoculant 'enhanced site occupier and rapid colonizer' within the tissues of plants (5) and endophyte product(s) that provide improved root, leaf, stem and or vegetative bud (flowers) growth to plants whilst reducing plant senescence to plants as well as (6) for the reduction of environmental or cultural stress to plants e.g. root loss due to trimming, pruning, cuttings, and seeding, transplanting, or other stresses with the net result of (7) improved crop quality, improved rooting, improved emergence/germination and faster development to marketability of the crop and further allows (8) the product(s) (as endophytes) can be formulated into value-added products that provides unique feature/benefits to provide natural induced plant resistance to fungal diseases such as powdery mildew, *botrytis*, root rots, seed seed decay, wilt diseases and or insects/mites.

(9) and endophyte product(s) that provide improved root, leaf, stem and or vegetative bud (flowers) growth to plants as well as

(10) A strain of *Clonostachys rosea* i.e. 88-710 with a unique genetic coding that differentiates the endophyte from other fungal strains of *Clonostachyus rosea* or *Gliocladium roseum*. e.g. a strain that does not produce the sexual state (teleomorph) as does the anamorph referred to as *Bionectria ochroleuca* which is morphologically indistinguishable from *C. rosea*.

(11) An endophyte *Clonostachys rosea* strain 88-710 acts as an inoculant to stimulate and have an additive effect with *rhizobium* on the production of nitrogen fixing nodules on legumes and growth enhancement e.g. beans, soybeans, peas, and alfalfa.

The invention relates to a process and method for the production and use of endophytes as plant inoculants products that provide unique inoculant feature/benefits for the promotion of plant vigor, health, growth and yield comprising the fungal group *Clonostachys rosea*. I also relates to a process and method for producing economically acceptable quantities of a fungal conidial preparation of *Clonostachys rosea* utilizing a discrete solid substrate fermentation system. The invention further relates to an endophyte product(s) produced by such processes and methods. Such a product may comprise *Clonostachys rosea*; strain 88-710 and the process for making the product(s) provide various levels of highly viable/stable spores and mycelia material in a stable formulation that prevents the degradation of a living endophyte *C. rosea* strain. The endophyte product(s) comprising *Clonostachys rosea*, strain 88-710 is unique in terms of genetic profile and as an endophyte the strain does not produce the sexual state (teleomorph) as does the anamorph referred to as *Bionectria ochroleuca* which is morphologically indistinguishable from *C. rosea*. The endophyte product(s) may comprise a solid substrate of, for example, certain cereals e.g. rye, which contain sufficient natural emulsifiers in the form of various proteins, lignans, to provide the *C. rosea* spores/mycelium production with excellent natural dispersing/wetting/sticker agents that allows for rapid site occupation on/in plants for use in EndoFine® formulations e.g. seed treatments, without having to add other emulsifiers for dispersion and use. The product formulation allows/enables practical use and application of the product(s) to roots, stems, leaves, flowers, bulbs, etc of plants as a water-based sprayable formulations or as a dusts for other uses e.g. seed treatment, dusts for insect/mite vectors. The product when applied to seeds, roots, stems, leaves, flowers, wounds or cut surfaces of plants enables the endophyte to act as an inoculant 'enhanced site occupier' within the tissues of plants. The product provides improved roots, leaf, stem and or vegetative bud (flowers) growth to plants and or enhances/improves the germination and emergence of seeds. The product provides for reduction of environmental or cultural stress to plants e.g. root loss due to trimming, pruning, cutting or other stresses. The product provides improved crop quality and faster development to marketability of the crop. The product provides for a reduction in the dependency on chemical pesticides for pest control e.g. control of *Botrytis, Fusarium, Pythium*, spp. and the like. The product can be used for the production of a variety of greenhouse, horticultural and agronomic field crops. The composition of the invention can be a plant inoculant composition comprising *Clonostachys rosea* spores, conidia or mycelia in admixture with an agrochemically acceptable diluent or carrier. The invention also relates to a method of enhancing growth, health vigor or yield of a plant which method comprises applying the plant inoculant composition of the invention to a plant or plant locus. The invention further relates to a method of combating a plant fungus which method comprises applying an antifungally effective amount of the composition of the invention to a harmful fungus by occupying the targeted infection site or habitat of said fungus or denying the food source of said fungus. The endophyte of the invention can comprise the endophyte *Clonostachys rosea* strain 88-170 which acts as an inoculant to stimulate and has an additive effect with *rhizobium* on production of nitrogen fixing nodules on legumes (e.g. beans, soybeans, peas, and alfalfa) and leads to growth enhancement. The endophyte of the invention when comprising *Clonostachys rosea* strain 88-710 provides wound healing benefits as an inoculant that can in turn, when formulated in suitable formulations, can provide additional/additive plant protective benefits against a wide range of plant diseases, insects and mites e.g. powdery mildew, two-spotted mites, aphids. The endophyte of the invention when comprising *Clonostachys rosea* strain 88-710 can be combined with rooting hormones such as indole-3-butyric acid (IBA) to provide inoculant plus rooting benefits to cuttings/transplants of plants. The endophyte *Clonostachys rosea* strain 88-710 can be combined with rooting hormones such as indole-3-butyric acid (IBA) to provide inoculant plus rooting benefits to cuttings/transplants of plants for use with robotic equipment in formulations that do not interrupt robotic sensing equipment by leaving sensor sensitive dust particles on plant material during transplanting.

The invention relates to a production and use process whereby endophytes as inoculant products specifically the example of strain 88.710 that provides for the enhanced promotion of plant vigor, health, growth and yield. The production method for producing the endophyte, *C. rosea* strain 88-710, provides for producing economically acceptable quantities of a fungal conidial preparation utilizing a discrete solid substrate fermentation system; the method also results in effective levels of inoculum in spore and mycelia in stable and practical/applicable product formulations. Specifically the endophyte e.g. *Clonostachys rosea*, formerly called *Gliocladium roseum*, as a specific strain 88-710, which is genetically and reproductively differentiated from other Clonostachys or *Gliocladium* strains, is used as an example for providing a high level of inoculant "site occupation" performance in plants that in turn provides for improved seed, leaf, stem, root growth and yield by reducing stress factors (environmental as well as cultural) in the growth of plants.

The invention also provides the novelty of an endophyte *Clonostachys rosea* strain 88-170 acting as an inoculant to stimulate and have an additive effect with *rhizobium* bacteria on the production of nitrogen fixing nodules on legumes and growth enhancement e.g. beans, soybeans, peas, and alfalfa.

The invention also provides unique use and novelty in that endophytes e.g. *Clonostachys rosea* strain 88-170 can be used/formulated to provide wound healing benefits that can in turn, when formulated with suitable salts, and natural emulsifiers (proteins, lactic acid), can provide additional/additive plant protective benefits against a wide range of plant diseases, insects and mites e.g. powdery mildew, two-spotted mites, aphids.

The rapid colonisation and use of formulated *Clonostachys rosea* strain 88-710, e.g. as the brand EndoFine®, provides production feature/benefits for plants in terms of, faster emergence/germination, shorter production time, faster harvesting and crop marketability and quality.

The invention applies to various plant species and agronomic crops e.g. roses, cucumbers, tomatoes, peppers, cereal crops, legumes, crucifers, etc. grown under greenhouse or field conditions under a variety of cultural methods e.g. hydroponics, seeds, cuttings, transplants, field cultivation, etc. Specific formulations of *Clonostachys rosea* provide unique inoculant benefits to plants that reduce plant stress to enhance over all plant growth, health, yield and quality including the preventive infection via induced plant resistance to plant/seed diseases and pests thereby reducing dependency on chemical pesticides for pest control.

DESCRIPTION OF THE DRAWINGS

FIG. 9 shows colonisation of rose plant shoots and roots using EndoFine alone and in combination with IBA rooting compound.

FIG. 10 shows root weight gains of rose plant roots and roots using EndoFine alone and in combination with IBA rooting compound.

DEFINITION OF TERMS

Figure 1:
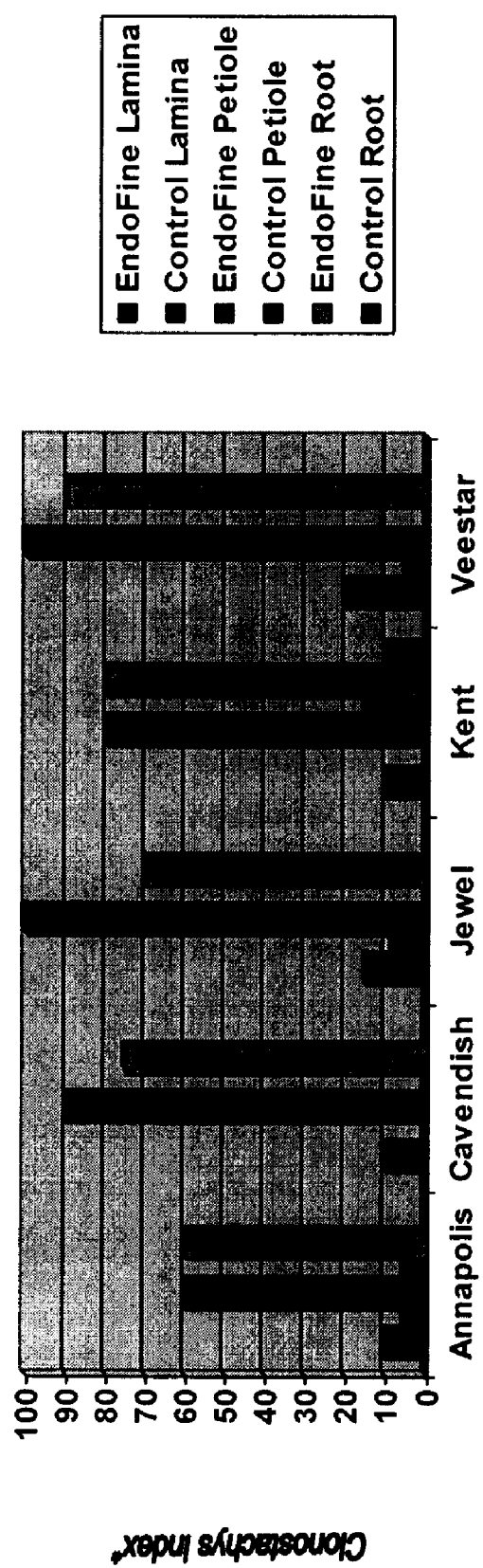
FIG. 1 shows sporulation of *Clonostachys* (EndoFine®) on tissues of strawberry plants that were treated by immersion in EndoFine suspension.

As employed above and throughout this disclosure, the following items unless otherwise indicated shall be understood to have the following meaning:

Endophyte is defined as "fungi or bacteria that form symptom less infections, for part or all of their life cycle within healthy leaves and stems of plants" (Definition by Hawksworth et al, 1995). This invention also indicates that the definition of endophytes such as *C. rosea* may also include living within plant roots and grow to be part the entire plant rhizosphere and have the ability to reduce or convert minerals into forms more easily absorbed by plants.

*Clonostachys rosea* formerly *Gliocladium roseum* is an endophyte fungus as defined in "Compendium of Soil Fungi" vol 1 Domsch, K. H., Gams, W and Anderson, Traute-Heidi Academic Press 1980 pgs 369-374.

A 'site occupier endophyte' is defined as meaning an endophyte (fungus/bacteria) that occupies the apoplast within cells i.e. within cell tissues/membranes.

Inoculant is defined as a beneficial microbe that promotes plant health, size, root growth or increases yield and aids in reducing or eliminating the use of chemical fungicides.

A legume nodule e.g. from beans, soybeans, peas, and alfalfa, that occur on the roots of plants that associate with symbiotic bacteria under nitrogen limiting conditions.

A symbiotic relationship is defined as a close, prolonged association between two or more different organisms of different species that may, but does not necessarily, benefit each member or a relationship of mutual benefit or dependence.

DETAILED DESCRIPTION OF THE INVENTION

The detailed description of the invention is detailed in summary of the invention (above) and in the claims.

The present invention provides a method and process for the production and use of:

(1) an effective plant inoculant of an endophyte product(s) produced comprising *Clonostachys rosea* strain 88-710 with unique inoculant feature/benefits for the promotion of improved plant vigor, health, quality, growth and yield (2) a process for making the product(s) that provides for various levels of highly viable/stable spores and mycelia material in stable but naturally emulsified formulations that prevents the degradation of a living endophyte *C. rosea* strain 88-710 while providing excellent dispersal characteristics.

(3) product formulations that allow/enables practical use and application of the product(s) to seeds, roots, stems, leaves, flowers, bulbs, etc of plants as a water based sprayable formulations, as a dusts or spore concentrates for other uses including application equipment/devices of practical use by growers e.g. seed treatment or insect vectoring, spray or irrigation equipment, (4) and allows the product(s) (endophyte) when applied to, seeds, roots, stems, leaves, flowers, wounds or cut surfaces of plants to act as an inoculant 'enhanced site occupier and rapid colonizer' within the tissues of plants (5) and endophyte product(s) that provide improved root, leaf, stem and or vegetative bud (flowers) growth whilst reducing plant senescence to plants as well as (6) for the reduction of environmental or cultural stress to plants e.g. root loss due to trimming, pruning, cuttings, and seeding, transplanting, or other stresses with the net result of (7) improved crop quality, improved rooting, improved emergence/germination and faster development to marketability of the crop and further allows (8) the product(s) (as endophytes) can be formulated into value-added products that provides unique feature/benefits to provide natural induced plant resistance to fungal diseases such as powdery mildew, *botrytis*, root rots, seed seed decay, wilt diseases and or insects/mites.

(9) and endophyte product(s) that provide improved root, leaf, stem and or vegetative bud (flowers) growth to plants as well as

(10) A strain of *Clonostachys rosea* i.e. 88-710 with a unique genetic coding that differentiates the endophyte from other fungal strains of *Clonostachyus rosea* or *Gliocladium roseum*. e.g. a strain that does not produce the sexual state (teleomorph) as does the anamorph referred to as *Bionectria ochroleuca* which is morphologically indistinguishable from *C. rosea*.

(11) An endophyte *Clonostachys rosea* strain 88-710 acts as an inoculant to stimulate and have an additive effect with *rhizobium* on the production of nitrogen fixing nodules on legumes and growth enhancement e.g. beans, soybeans, peas, and alfalfa.

Examples 1 to 3 (below) summarize the method for producing and preparing a stable effective (colonising) endophyte inoculant product containing *Clonostachys rosea* strain 88-710.

Example 4 details the means by which the endophyte *C. rosea* when applied as an inoculant allows the inoculant to act as an 'enhanced site occupier' within the tissues of plants. This action in turn provides for improved plant growth of roots, leaf, stem, and/or vegetative bud growth (flowers or fruit) as illustrated in examples 5 and 6. In Tables 1 and 4, and 5 trials (commercial greenhouse operations involving over 150,000 potted miniature rose plants) demonstrated the consistent activity of *C. rosea* to improve quality of production in terms of more flower buds, less senescent leaves and shorter growth period for marketability.

Examples 7 to 11, illustrate the reduction of environmental or cultural stress to plants e.g. root loss due to trimming, pruning, cuttings, seeding, transplanting, or other stresses with the net result of (7) improved crop quality and faster development to marketability of the crop. Pruning of rose plants to stimulate bud development usually results in a 40-50% loss of net root mass; the resulting stress to the plants causes the plants to produce sugars to compensate for the trimming stress (note: similar effects occur to plants from various environmental or cultural stresses). This in turn makes roots susceptible to root diseases e.g. *fusarium, pythium. C. rosea* acts as an inoculant "site occupier" to prevent the sugars from being consumed by harmful plant pathogens and in this way allows the sugar reserves of the plant to maintain existing root mass and promote faster vegetative stem and leaf growth . . . hence faster yield, marketability and higher quality plants.

Preparation of a Stable Effective Endophyte Inoculant Product Containing *Clonostachys rosea*

EXAMPLE 1

The unique method of preparation and know-how linked to the performance claims in this invention involves identifying performance standards that produce: **

** (also note references: Schroeder's, H. J. Samuels, G. J., Siefert, K. A. & Gams, W. (1999) Classification of the myoparasite *Giocladium roseum* in *Clonostachys* as *C. rosea*, its relationship to *Bionectria ochroleuca* and notes on other *Gliocaldium* like fungi. Mycologia 91, 365-383. Domsch, K. H., Gams, W., Anderson, Traute-Heide (1980) Compendium of Soil Fungi Volume 1, Academic Press, A Subsidiary of Harcourt Brace Jovanovich, Publishers)

(1) A percent acceptable recovery method of a minimum of 60% conidia/viable spores from a solid matrix.

(2) An analytical range: of 0.1 to 5×10 to the $9^{th}$ (or higher) CFU for pure inoculum powder (concentrate). Preferred concentrations range from $10^4$ to $10^{12}$ CFU/gram, especially from $10^6$ to $10^{10}$ CFU/gram, particularly from $10^7$ to $10^{10}$ CFU/gram, and more especially from $10^7$ to $10^9$ CFU/gram.

(3) A method to measure a minimum limit of quantification of 2 to 3.7×10 to the $8^{th}$ CFU/gram (or higher) for finished end-use formulation. Finished end-use formulations usually are diluted by admixture with an agrochemically acceptable diluent. Dilution can be anything from 2 to ten thousandfold (usually) though dilutions of between 10 and a thousandfold are more preferred and dilutions of 15 to 100 times are especially preferred in most situations.

(4) A limited of detection for viable spores of 0.1 to 5×10 to the $9^{th}$ and higher (5) % CV repeatability: 85% (within lab) or higher (6) % CV reproducibility (between lab) 85% or higher Production of Viable Conidia by Solid Substrate Fermentation The preparation of a stable and effective endophyte inoculant containing of *Clonostachys rosea* involves cultivation of *Clonostachys rosea* cells on a solid substrate. Preparation of Fresh Vegetative or Conidial Cultures of *C. Rosea* (Inoculum), is Carried Out by incubating a pure culture on a suitable nutrient media such as Potato Dextrose Agar or Malt Extract Agar (PDA source is from Adjuvants Plus Inc., Malt Extract can be obtained from one or more commercial suppliers), and allowing the cultures to incubate/sporulate for about 7-20 days depending on temperature and humidity. Alternatively, cultures may be transferred to one or more liquid or solid substrate media such as cereal grain, nutrient enriched vermiculite or other solid matrix, and allowed to colonize said substrate in order to facilitate improved dispersion during inoculation.

A particulate material (or a mixture thereof) capable of holding sufficient moisture and nutrients required to sustain the growth and promote sporulation of *C. rosea* cultures is introduced into a rotary blender capable of achieving and maintaining temperatures and pressures required for sterilizing material. A typical mixture contains a cereal grain or other solid substrate, such as rye, millet, or vermiculite, chalk or gypsum and sufficient water to produce a finished product containing approximately 45-55% moisture and a pH between 6.6 and 7.6. A unique feature in this invention) of the solid substrate, is that certain cereals e.g. rye, contain sufficient natural emulsifiers in the form of various proteins, lignans, to provide the *C. rosea* spores with excellent natural dispersing/wetting/sticker agents for use in EndoFine® formulations e.g. seed treatments.

The nutrient mixture is blended and sterilized by heating to approximately 125° C. and maintained at this temperature for 20-45 minutes as necessary to achieve adequate sterilization. The sterilized mixture is permitted to cool to a temperature below 50° C. and *C. rosea* inoculum as described above, is introduced aseptically into the blending vessel. Once introduced, the inoculum is thoroughly mixed and dispersed throughout the sterile substrate material, connected to a bag filling system by means of a sterile connector and filled into sterile polyethylene bags containing microporus breathing strip. The filled bags are immediately sealed in a clean room, and transferred to a suitable growing environment for incubation and allowed to grow to maturity.

Alternatively, the particulate material can be premixed, introduced into bags, trays or other suitable containers and sterilized insitu. The sterile particulate substrate can then be admixed with a suitable *C. rosea* inoculum and allowed to grow to maturity. Prepared and inoculated substrate, in bags is incubated at room temperature 18-24° C. until the substrate is densely colonized with mycelium of *C. rosea* (about 6 days); care is taken to allow for air exchange, to eliminate excess water from bags and allow for even growth of mycelium over a period of 7-28 days depending on conditions. Continued incubation produces spores of the fungus with 6-10 weeks of inoculation depending on growing conditions. The colonized substrate may be periodically shaken to insure the uniformity of growth, promote sporulation and maximize productivity.

After sporulation, the colonized grain is ground and the product is sorted via a vibratory sieved into 100, 40 or various mesh sizes; various mesh sizes are used to prepare final formulations depending on uses. The final concentrate of 100, 40 or various mesh sizes of should contain a minimum of 10 to the $10^{th}$ viable CFU (colony forming units) spores/gram.

A Novel Method for Measuring the Number of Viable Spores per Gram of Product

EXAMPLE 2

The invention also involved developing a consistent method for determining the viable number of spores per gram of powder (CFU spores/g). This was done by place 0.1 g powder in 9.9 ml sterile distilled water in a sterile test tube. (=10 minus 2 dilution). Shake thoroughly, and continuing the dilution series with 1.0 ml in 9.0 ml each time. Zero point one ml (0.1 ml) of each dilution is then onto PDTSA (in-house source from Adjuvants Plus Inc.) in Petri dishes at least 3 replicates. The Petri dishes are then incubated for 4-5 days until colonies have developed, and count the colonies. Multiply the colony count by the dilution factor to give number of viable (colony-producing) spores per gram powder. For example, the first dilution of 10 to minus 2 becomes 10 to 3 because only 0.1 was used for plating, so in this instance multiply the colony by 1000.

For determining the number of viable spores per gram of grain substrate, 1 g of dried grain is sampled randomly from stored inoculum. The grains are shaken in sterilized distilled water plus surfactant (in source Adjuvants Plus Inc.) at 110 rpm for 10 min., filter the spore suspension through 3 layers of cheesecloth, estimate the spore concentration with aid of hemacytometer, and continue the dilution series with 1.0 ml in 9.0 ml each time if needed.

Preparation of Stable Useful Product Formulations of C. Rosea

EXAMPLE 3

All living fungal/bacterial endophytes are highly susceptible to degradation due to a number of factors e.g. high temperatures (4° C. or higher), halogens in water e.g. chlorinated water, bacterial contamination, etc. This invention also involves the preparation of a novel formulation that provides stability for viable spores and the formulation of the products for practical use and application to roots, stems, leaves, flowers, bulbs, etc of plants as a water based sprayable formulations or as a dusts for other uses e.g. seed treatment.

The objective with final formulations is to have stable viable spores in the finished product at various desired levels i.e. from 0.1 to minimums of $2\times10^7$ spores/g. or higher. The fine powder of concentrated C. rosea (100 mesh) is mixed with an inert carrier (calcium carbonate 15-30% w/w; talc 13-15% w/w and sodium dibutylnaphthalene sulfonate (75-78% w/w and, sodium sulfate 13-20% w/w) for a product example EndoFine® of 14.5% w/w concentrate powder of C. rosea: 85% w/w carbonate/talc: 0.5% sodium dibutylnaphthalene sulfonate mix w/w.

Different EndoFine products can also be made from the C. rosea concentrate e.g. $2.5\times10$ to the $8^{th}$ CFU/g or higher for adequate delivery on seeds and other formulations for a variety of uses.

Basically, the mixing rate is determined by the density of spores of C. rosea contained in powder product. The finished product(s) can be stored in waterproof containers at 4° C. for a period of 1 year or more before usage (see example 14). Product can also be moved in and out of refrigerated storage and kept at room temperatures for minimum periods without affecting degradation or viability of C. rosea in the finished formulation.

The Endophyte C. rosea as an Inoculant to Act as and Enhanced Site Occupier within Tissues of Plants and Imparting Plant Inoculant Resistance to Diseases, Insects and Mites

EXAMPLE 4

The sampling of leaf, stem and root tissue of treated plants from various crops e.g. roses (both field and greenhouse crops see Tables 1 to 10, have indicated that product applications of C. rosea (prepared as outlined above), are able to penetrate and colonize stems, leaves and roots. The sampling also indicated that C. rosea was able to grow rapidly in naturally senescent or stressed tissues of plants and continue to sporulate after treatment. In Tables 1 and 2 (below). Endophytic development of Clonostachys rosea, strain 88-710, was established in treated rose plants of all treatments at all sampling times i.e. C. rosea was present inside leaves, stems, and roots. C. rosea was also present in senescent leaves. No other pathogenic organisms were recovered from leaves and stems incubated in the laboratory e.g. Botrytis cinerea or Alternaria alternate i.e. the trials were completed in the absence or near absence of disease to demonstrate inoculant feature/benefits.

Tables 8-10 (below) illustrate the colonization of C. rosea strain 88-710 on various varieties of strawberries as an immersion treatment to transplants that were subsequently grown in the greenhouse to maturity. Growth differences as measured in dry mass (all strawberry varieties) treated with EndoFine® was 122% over untreated plants. Table 9 illustrates the ability of Clonostachys rosea, strain 88-710 to impart natural plant resistance to diseases to treated plants Vs. untreated plants e.g. botrytis in strawberries after a transplant dip treatment (also see example 18, Table 18 re protection against powdery mildews, insects and mites).

The Endophyte Product of C. rosea Providing Improved Seed Growth, Germination, Root, Leaf, Stem and or Vegetative Bud (Flower) Growth to Plants and Improved Quality The following examples (Tables 1 to 13, and 19) demonstrate the use of Clonostachys rosea, strain 88-710 for providing improved seed germination, seed, root, stem and or vegetative growth benefits to plants and improved crop quality/harvest and yield.

EXAMPLE 5

TABLE 1

Trials on rose varieties**; number of flowers, flower buds, percent of dead or senescent leaves and quality index in miniature roses treated with Clonostachys rosea at 80 days after planting (treatments at rates of 15 g/Litre of finished product ($2 \times 10^7$ spores/g of fresh cuttings, planted cuttings, first trimming, second trimming or combinations thereof). The treatment in the table below has been replicated 8 times for various rose varieties in commercial greenhouse trials involving over 50,000 planting pots (4 inches in diameter each containing 4 plants).

| Treatment timing | Flower buds (number/pot) | Open flowers (number/plot) | Senescent/dead leaves (%) | Quality index |
|---|---|---|---|---|
| 1. Not treated | $8.3^c$ | $1.3^{c2}$ | $10.3^2$ | 5 |
| 2. Fresh cuttings (FC) | $11.3^{bc}$ | $2.3^{bc}$ | $4.7^{bc}$ | 7 |
| 3. Planted cuttings (PC) | $9.0^c$ | $1.3^c$ | $8.0^{ab}$ | 7 |
| 4. First trimming (FT) | $10.7^c$ | $3.3^{ab}$ | $4.3^c$ | 7 |
| 5. Second trimming (ST) | $15.0^{ab}$ | $1.7^c$ | $4.3^c$ | 8 |
| 6. FC + FT | $10.0^c$ | $1.0^c$ | $5.0^{bc}$ | 8 |
| 7. FC + ST | $15.7^a$ | $4.0^{ab}$ | $3.3^c$ | 8 |
| 8. FC + FT + ST | $14.0^{ab}$ | $6.3^a$ | $1.3^d$ | 10 |
| 9. PC + FT | $15.3^{ab}$ | $3.0^{bc}$ | $4.3^c$ | 9 |

TABLE 1-continued

Trials on rose varieties**; number of flowers, flower buds, percent of dead or senescent leaves and quality index in miniature roses treated with *Clonostachys rosea* at 80 days after planting (treatments at rates of 15 g/Litre of finished product ($2 \times 10^7$ spores/g of fresh cuttings, planted cuttings, first trimming, second trimming or combinations thereof). The treatment in the table below has been replicated 8 times for various rose varieties in commercial greenhouse trials involving over 50,000 planting pots (4 inches in diameter each containing 4 plants).

| Treatment timing | Flower buds (number/pot) | Open flowers (number/plot) | Senescent/dead leaves (%) | Quality index |
|---|---|---|---|---|
| 10. PC + ST | $15.7^a$ | $4.7^{ab}$ | $4.0^c$ | 9 |
| 11. PC + FT + ST | $17.7^a$ | $5.3^a$ | $1.3^d$ | 10 |

Values followed by the same letter are not significantly different (PLSD, p > 0.05)
** roses (Parade series, Padio Hit, Town and Country, Courtyard, Vigorosa, Flower Circus. Climbing Max, various cultivars from Denmark, Germany)

EXAMPLE 6

In Tables 2 and 3 (below), experiments were initiated when roots of hydroponic pepper plants had grown 5-8 cm upstream and downstream from the rockwool plugs in the baskets, and before roots of adjacent plants made contact. For treatments, each beneficial microbe was added to the nutrient solution in the reservoir of each of four replicate hydroponic units. Final density of the bacteria was $10^7$ cells $mL^{-1}$ of the total nutrient solution in the unit. *C. rosea* density was $10^6$ spores $mL^{-1}$ of total nutrient solution.

TABLE 2

Effects of beneficial microbes on growth of pepper plants in small-scale hydroponic trough systems with treatments of *C. rosea*

| Treatment | Root volume (mL) | Root fresh mass (g) | Root dry mass (g) | Leaf area (cm$^2$) | Plant height (cm) | Shoot fresh mass (g) |
|---|---|---|---|---|---|---|
| Control | 10.5 b | 4.7 b | 0.27 b | 1410 b | 33.7 b | 57 b |
| *Ps. chlororaphis* Tx-1 | 14.9 a | 7.1 a | 0.44 a | 1667 a | 40.2 a | 66 ab |
| *Ps. fluorescens* 63-28 | 16.4 a | 7.5 a | 0.45 a | 1515 ab | 41.7 a | 69 a |
| *C. rosea* 88-710 | 17.3 a | 8.2 a | 0.51 a | 1743 a | 42.0 a | 75 a |

Means in a column followed by the same letter are not significantly different (protected LSD, P < 0.05).

TABLE 3

Effects of beneficial microbes on growth of pepper plants in small-scale hydroponic trough systems.

| Treatment | Root volume (mL) | Root fresh mass (g) | Root dry mass (g) | Leaf area (cm$^2$) | Plant height (cm) | Shoot fresh mass (g) |
|---|---|---|---|---|---|---|
| Control | 25 a | 20.7 b | 1.35 a | 2055 c | 51 b | 136 b |
| *Ps. chlororaphis* Tx-1 | 27 a | 21.8 b | 1.30 a | 2419 b | 55 ab | 138 b |
| *Ps. fluorescens* 63-28 | 28 a | 23.9 ab | 1.37 a | 2666 a | 60 a | 146 a |
| *C. rosea* 88-710 | 29 a | 24.6 a | 1.41 a | 2714 a | 61 a | 144 ab |

Means in a column followed by the same letter are not significantly different (protected LSD, P < 0.05).

The Endophyte Product of *C. rosea* Providing for Improved Crop Quality and Faster Development to Marketability.

EXAMPLE 7

TABLE 4

Commercial greenhouse trials on varies rose varieties; Effects of *Clonostachys rosea* treatments on numbers of flower buds and open flowers, percent senescent/dead foliage, and plant appearance quality in miniature roses at 80 days after cuttings were planted. Treatments were at rates of 10 g/Litre of finished product ($2 \times 10^7$ spores/g) of fresh cuttings, planted cuttings, first trimming, second trimming on 50,000 (4 inch) rose pots each containing 4 plants.

| Treatment timing | Flower buds (no. per pot) | Open flowers (no. per pot) | Senescent/dead leaves (%) | Quality index (1-10)$^a$ |
|---|---|---|---|---|
| 1. Not treated | $7.6^c$ | $1.7^c$ | $15.0^a$ | 4 |
| 2. Fresh cuttings (FC) | $10.7^{bc}$ | $3.3^{bc}$ | $5.4^{bc}$ | 7 |

TABLE 4-continued

Commercial greenhouse trials on varies rose varieties; Effects of
*Clonostachys rosea* treatments on numbers of flower buds and open flowers, percent
senescent/dead foliage, and plant appearance quality in miniature roses at 80 days
after cuttings were planted. Treatments were at rates of 10 g/Litre of finished
product ($2 \times 10^7$ spores/g) of fresh cuttings, planted cuttings, first trimming, second
trimming on 50,000 (4 inch) rose pots each containing 4 plants.

| Treatment timing | Flower buds (no. per pot) | Open flowers (no. per pot) | Senescent/dead leaves (%) | Quality index $(1-10)^a$ |
|---|---|---|---|---|
| 3. Planted cuttings (PC) | $9.3^{bc}$ | $2.7^c$ | $6.7^{bc}$ | 7 |
| 4. First trimming (FT) | $11.0^{bc}$ | $4.7^{ab}$ | $4.0^c$ | 8 |
| 5. Second trimming (ST) | $14.0^{ab}$ | $3.3^{bc}$ | $4.0^c$ | 8 |
| 6. FC + FT | $11.7^b$ | $4.3^{abc}$ | $3.7^c$ | 8 |
| 7. FC + ST | $15.0^a$ | $5.7^{ab}$ | $3.0^{cd}$ | 9 |
| 8. FC + FT + ST | $15.0^a$ | $7.0^a$ | $0.7^d$ | 10 |
| 9. PC + FT | $15.3^a$ | $4.0^{bc}$ | $3.7^c$ | 9 |
| 10. PC + ST | $14.7^a$ | $6.0^{ab}$ | $3.0^c$ | 9 |
| 11. PC + FT + ST | $17.0^a$ | $6.7^a$ | $1.0^d$ | 10 |

$^a$Considers appearance of foliage and flowers; 1 = very poor, 10 = excellent. All plants in a treatment assessed collectively.

EXAMPLE 8

TABLE 5

Trials on rose varieties; Average Number of the flowers, flower buds,
percent of dead or senescent leaf and quality index in miniature roses treated with
*Clonostachys rosea* at 80 days after planting. Treatments with $2 \times 10^7$
spores/g at rates of 5 g/Litre at first trimming, second trimming; a total of
50,000 (4 inch Size) rose pots were treated each containing 4 rose plants.

| Treatment timing | Flower buds (number/pot) | Open flowers (number/plot) | Senescent/dead leaves (%) | Quality index |
|---|---|---|---|---|
| 1. Not treated | 8.0 | 1.5 | 12.0 | 5.0 |
| 2. First Trimming (FT) | 11.0 | 3.4 | 3.0 | 7.5 |
| 3. Second Trimming (ST)* ready to ship at 65 days | 15.0 | 2.9 | 4.0 | 8.0 |

These assessments in Tables 1, 4 and 5 coincided with the general time at which the grower would ship the plants to buyers. The data on the numbers of flower buds and open flowers underscored the immense beneficial impact of *Clonostachys rosea* in promoting earlier and better flowering, healthier plants and improved vegetative growth.

The Treated Plants were Shipping-Ready 10-15 Days Before the Untreated Plants.

EXAMPLE 9

TABLE 6

In replicated treatments on hydroponic cucumbers the following
treatments were conducted for various inoculants.

| | Treatments | Concentrations | Experiments* 1 | 2 | 3 |
|---|---|---|---|---|---|
| 1 | *Pseudomonas chlororaphis* Tx-1 (Spotless) | $10^6$ cfu/mL | X | X | X |
| 2 | *Pseudomonas fluorescens* 63-28 (AtEze) (= *Pseudomonas chlororaphis* 63-28) | $10^6$ cfu/mL | X | X | X |
| 3 | *Clonostachys rosea* (EndoFine ®) | $10^6$ cfu/mL | X | X | X |
| 4 | *Trichoderma harzianum* (PlantShield) | $10^6$ cfu/mL | X | X | X |
| 5 | *Bacillus cereus* HY06 | $10^6$ cfu/mL | X | | X |
| 6 | *Bacillus subtilis* GB03 (Companion) | $10^6$ cfu/mL | | X | X |
| 7 | *Streptomyces griseoviridis* K61 (Mycostop) | 0.05 g/L | | X | X |
| 8 | Chitosan | 0.05 g/L | | X | |
| 9 | Fish hydrolyzate ('Drammatic') | 15 mL/L | | X | X |
| 10 | Controls (not treated) | — | | | |

*Experiments 1, 2, and 3, respectively were conducted in spring/summer, fall, and winter/spring crop periods.

*EndoFine is a registered Trademark of Adjuvants Plus Inc.

TABLE 7

Effects of four microbial agents/products applied once (1), twice (2), or three times (3) to the root zone of cucumber plants on fruit yield in the spring/summer experiment.

| Agents/products | Number of applications | No. of fruit/30 plants | p-value[1] | Yield Change(%)[2] |
|---|---|---|---|---|
| None (control) | — | 1069.7bc | | |
| Pseudomonas chlororaphis 63-28 (AtEze) | 1 | 1048.3bc[3] | 0.579 | −2% |
| | 2 | 1136.3ab | 0.096 | +6.3% |
| | | 1181.9a | 0.007 | +10.5% |
| Bacillus subtilis | 1 | 1054.0bc | 0.683 | −1.4% |
| | 2 | 1000.0c | 0.071 | −6.5% |
| | 3 | 1147.7ab | 0.051 | +7.3% |
| C. rosea* strain 88-710 | 1 | 1171.0ab | 0.013 | +9.5% |
| | 2 | 1117.3ab | 0.221 | +4.5% |
| | 3 | 1188.7a | 0.005 | +11.1% |
| Trichoderma harzianum | 1 | 1121.3ab | 0.096 | +4.9% |
| | 2 | 1161.7a | 0.023 | +8.6% |
| | 3 | 1063.0bc | 0.867 | −0.06% |

[1]F-test contrast between treatment and control
[2]Yield change relative to the control
[3]Values followed by the same letter are not significantly different (T-grouping LSD, $p < 0.05$)
*EndoFine ® a registered trademark of Adjuvants Plus Inc. FIG. 1 shows sporulation of Clonostachys (EndoFine ®) on tissues of strawberry plants that were treated by immersion in EndoFine suspension for 2 minutes, planted in pots and sampled 15 days later. Plants were treated with 10 g EndoFine ®/L
* Sporulation of Clonostachys on the senescent/dead tissues (0-100 scales) Clonostachys was well-established in the leaf petioles and roots of treated plants of all of the tested cultivars (index values 60-100). The leaf laminae were only lightly colonized (10-20), but these were mostly new tissues that had grown AFTER the immersion treatment.

TABLE 8

Sporulation of Clonostachys (EndoFine ®) and Botrytis on tissues of strawberry plants that were treated by immersion in EndoFine suspension for 2 minutes, planted in pots and sampled 15 days later.

| Cultivar | EndoFine treatment[1] | Clonostachys index[2] Lamina | Petiole | Root | Botrytis index[3] Lamina | Petiole | Root |
|---|---|---|---|---|---|---|---|
| Annapolis | − | 5 | 5 | 0 | 10 | 55 | 0 |
| | + | 10 | 60 | 60 | 0 | 20 | 0 |
| Cavendish | − | 0 | 0 | 0 | 0 | 60 | 0 |
| | + | 10 | 90 | 75 | 0 | 20 | 0 |
| Jewel | − | 8 | 0 | 0 | 10 | 35 | 0 |
| | + | 15 | 100 | 70 | 0 | 0 | 0 |
| Kent | − | 0 | 15 | 10 | 0 | 30 | 0 |
| | + | 10 | 80 | 80 | 5 | 5 | 0 |
| Veestar | − | 5 | 0 | 0 | 0 | 25 | 0 |
| | + | 20 | 100 | 90 | 0 | 0 | 0 |

− untreated (Control)
+ treated with EndoFine ® suspension
[1]10 g EndoFine ®/L
[2]Sporulation of Clonostachys on the senescent/dead tissues (0-100 scales)
[3]Sporulation of Botrytis on the senescent/dead tissues (0-100 scales)

TABLE 9**

Effects of EndoFine ® (C. rosea) on growth components of strawberry dipped in EndoFine ® suspension before transplanting and grown in greenhouse at 77 days. Strawberry varieties treated with 20-8-20 fertilizer every 7 days at 25-100 g/100 L.

| Cultivar | EndoFine treatment[1] | Number of Runner | Length of runner (cm) | Average Dry mass (g) Root | Shoot | Crown |
|---|---|---|---|---|---|---|
| Annapolis | − | 2 | 60.5 | 1.03 | 2.07 | 1.31 |
| | + | 5 | 51.6 | 1.58 | 6.03 | 1.52 |
| Cavendish | − | / | / | 0.69 | 2.06 | 0.79 |
| | + | / | / | 1.22 | 4.19 | 2.28 |
| Jewel | − | / | / | 0.39 | 0.24 | 0.77 |
| | + | 1 | 66.8 | 0.59 | 4.91 | 0.71 |
| Veestar | − | 1 | 32.7 | 0.66 | 2.01 | 0.63 |
| | + | 2 | 50.25 | 0.93 | 3.34 | 0.76 |

− untreated (control)
+ treated with EndoFine ®/not available
[1]10 g/1 L EndoFine ®
**Differences in dry mass (all strawberry varieties) treated with EndoFine ® over untreated: 122%

Figure 1A:
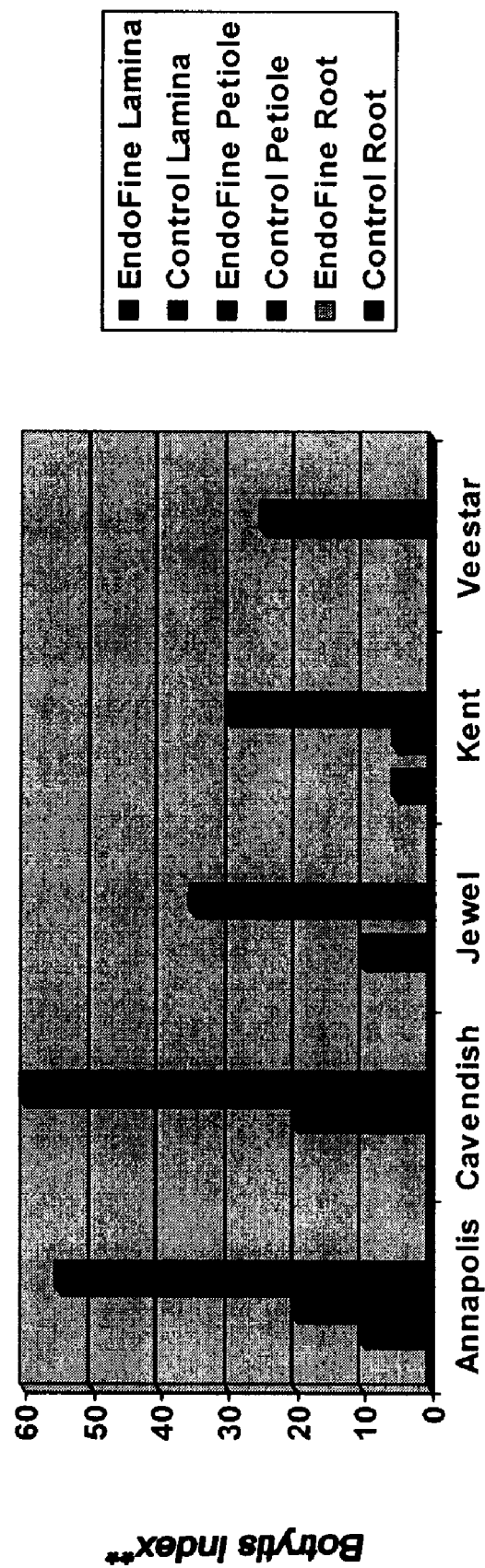
FIG. 1a shows sporulation of *Botrytis* on tissues of strawberry plants that were treated by immersion in EndoFine suspension for 2 minutes planted in pots and sampled 15 days later *Botrytis* on tissues of Strawberry Plants. Plants were treated with 10 g EndoFine®/L.

FIG. 1a shows sporulation of Botrytis on tissues of strawberry plants that were treated by immersion in EndoFine suspension for 2 minutes planted in pots and sampled 15 days later Botrytis on tissues of Strawberry Plants. Plants were treated with 10 g EndoFine®/L. All Botrytis found in the plant tissues would have been from natural sources (chiefly in the field). Index values indicated that leaf petioles of untreated plants were moderately infected with Botrytis (25-60), and the leaf laminae lightly infected (5-10) or not infected ((0). Much less Botrytis was found in petioles of treated plants (0-20) than in petioles of untreated plants (25-60). No Botrytis was found in roots of untreated or treated plants The Endophyte Product of C. rosea Providing for a Reduction of Environmental or Cultural Stresses to Plants

EXAMPLE 10

In a growth chamber experiment to study the ability of the endophyte C. rosea to withstand environmental and cultural stresses, miniature rose treated plants taken from treatments (see Table 1) were subjected to 2-3 days of limited soil moisture, or given regular watering/plant nutrient solution. The result was that the untreated plants wilted much more severely than treated plants with C. rosea under conditions of limited root zone moisture. Plants also took longer to recover in the case of untreated plants.

EXAMPLE 11

Stress Due to Trimming

TABLE 10

Percent root mass measurements for several rose varieties (Andrea,) 10 days after trimming. Treatments with 10 g/Litre of finished product containing $2 \times 10^7$ spores/g of C. rosea. The results below were replicated in approximately 50,000-planted pots (4 inch) in diameter each containing 4 rose plants.

| Treatment timing | % root mass reduction First trim | % root mass reduction second trim | Quality Index |
|---|---|---|---|
| 1. Not treated and trimmed (controls) | 75% | 70% | 4.5 |
| 2. First Trimming (FT) Treated | 25% | 20% | 7.5 |
| 3. Second Trimming (ST) Treated; ready to ship at 65 days | 25% | 15% | 8.0 |

EXAMPLE 12

TABLE 11

Barley seed treatment field trial for increasing tillering/heads and yield

| Treatment: (seeds) | # heads showing per meter of row | % Difference over untreated | Kg Yield | % difference over untreated |
|---|---|---|---|---|
| EndoFine 5 g/kg | 20.3 | 65% | 5302.7 | 28% |
| Apron 0.4 mg/kg | 15.8 | 28% | 4807.9 | 16% |
| Untreated | 12.3 | na | 4139.6 | na |

The Endophyte Product of C. rosea, Strain 88-710 as an Aid to Stimulate the Production of Nitrogen Fixing Nodules in Legumes for an Additive Growth Effect to *Rhizobium* Bacteria Tables 12, 14 and 16 demonstrate the ability of *Clonostachys rosea* strain 88-710 to act as a seed treatment inoculant to stimulate and have an additive effect with *rhizobium* on the production of nitrogen fixing nodules on legumes and growth enhancement e.g. beans, soybeans, peas, and alfalfa.

EXAMPLE 13

TABLE 12

Title: Field strip trial seed treatment Field Peas, EndoFine seed treatment 2005 Lethbridge Alberta
Variety: Eclipse
All seed treated with Phiom Bios Tag Team (*Pencillium* and *Mesorhizobium*) 1360 kg/bag of product
EndoFine seed treatment: 5 g/10 kg of seed A) Plant Emergence**

| Treatment | Plants/sq meter | % Difference over untreated |
|---|---|---|
| EndoFine | 48 | 108.7% |
| VitaFlo | 36 | 56.5% |
| Untreated | 23 | an |

TABLE 12-continued

Title: Field strip trial seed treatment Field Peas, EndoFine seed treatment 2005 Lethbridge Alberta
Variety: Eclipse
All seed treated with Phiom Bios Tag Team (*Pencillium* and *Mesorhizobium*) 1360 kg/bag of product
EndoFine seed treatment: 5 g/10 kg of seed B) Yield

| | Bushels/acre (27.2 kg/bu) | % Difference over untreated |
|---|---|---|
| EndoFine | 70 | 16.6% |
| VitaFlo | 66 | 1.7% |
| Untreated | 65 | an |

**Plants also shoed increased nodulation by 35% over untreated

Formulations of *Clonostachyus rosea*, Strain 88-710 Show Excellent Shelf Life and Stability Table 13 illustrates the shelf life and stability of C. raised strain 88-710 and the formulated product Endowing® went stored in a refrigerator at 4° C.

EXAMPLE 14

TABLE 13

Density of viable conidia of *Clinostats rose* (strain 88-710) in an End fine ® formulation stored in a refrigerator at 4° C.**

| Months of storage | Density of conidia (CFU/g) |
|---|---|
| 0 | $4.9 \times 10^7$ |
| 2 | $4.3 \times 10^7$ |
| 3 | $5.1 \times 10^7$ |
| 4 | $5.1 \times 10^7$ |
| 5 | $5.0 \times 10^7$ |
| 6 | $5.1 \times 10^7$ |
| 7 | $4.9 \times 10^7$ |
| 8 | $4.1 \times 10^7$ |
| 11 & 12 | $3.5 \times 10^7$ |

**EndoFine product is over formulated to compensate for any minor loss of spores and has a label guarantee of 2 × 10 to the $7^{th}$ CFU/g spores.

EXAMPLE 15

TABLE 14

Title: Grower Field Trial nitrogen fixation and growth benefits with EndoFine
Variety: AC Kent
Seeding date: Jun. 3, 2006; planted into corn stubble no fertilizer
Seed treatment: only EndoFine; no *Rhizobium*
EndoFine seed treatment: 0.5 g/kg of seed
Harvest dates: a) EndoFine Oct. 15, 2006
b) untreated Nov. 1, 2006
Multiple randomized samples

| Treatment | | % Difference over untreated |
|---|---|---|
| (A) Average root weight (Fresh) per plant (grams) | | |
| EndoFine | 4.82 | 17.6% |
| Untreated | 4.10 | na |
| (B) Average plant height inches | | |
| EndoFine | 35.52 inches | 5.1% |
| Untreated | 33.8 inches | na |
| (C) Average number of pods per plant | | |
| EndoFine | 21.72 | 20.1% |
| Untreated | 18.08 | na |

TABLE 14-continued

Title: Grower Field Trial nitrogen fixation and
growth benefits with EndoFine
Variety: AC Kent
Seeding date: Jun. 3, 2006; planted into corn stubble no fertilizer
Seed treatment: only EndoFine; no *Rhizobium*
EndoFine seed treatment: 0.5 g/kg of seed
Harvest dates: a) EndoFine Oct. 15, 2006
b) untreated Nov. 1, 2006
Multiple randomized samples

| Treatment | | % Difference over untreated | |
|---|---|---|---|
| (D) Average number of nitrogen fixing nodules per plant | | | |
| EndoFine | 24.48 | 29.5% | |
| Untreated | 18.9 | na | |
| (E) Average Fresh weight per plant (Grams) | | | |
| EndoFine | 57.0 | 10.5% | |
| Untreated | 51.6 | na | |
| (F) Harvest dates (days earlier Vs Untreated) | | | |
| EndoFine | 15 days | | |
| (G) Average yield (bu/acre) | | | |
| EndoFine | 44.58 bushels/acre | 15.4% | EndoFine treated soybeans harvested 15 days Earlier than untreated soybeans. |
| Untreated | 38.62 bushels/acre | | |

*Clonostachys rosea*, Strain 88-710 as an Inoculant for the Uptake of Nitrogen, Phosphate and Potassium Nutrient Solutions.

Figure 2:
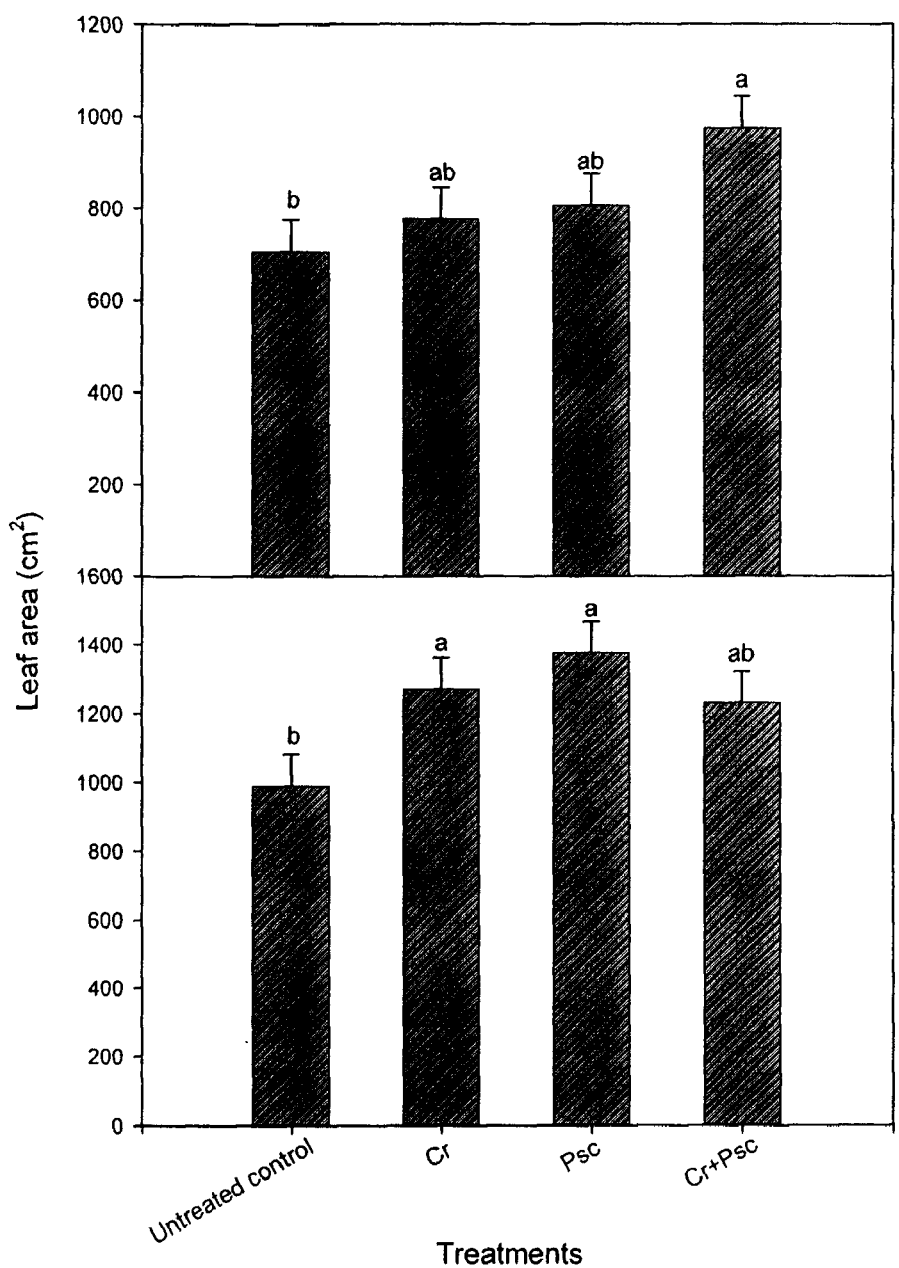
FIG. 2 shows the effects of *Clonostachys rosea* and *Pseudomonas chlorographis* on leaf area of cucumber.
Figure 3:
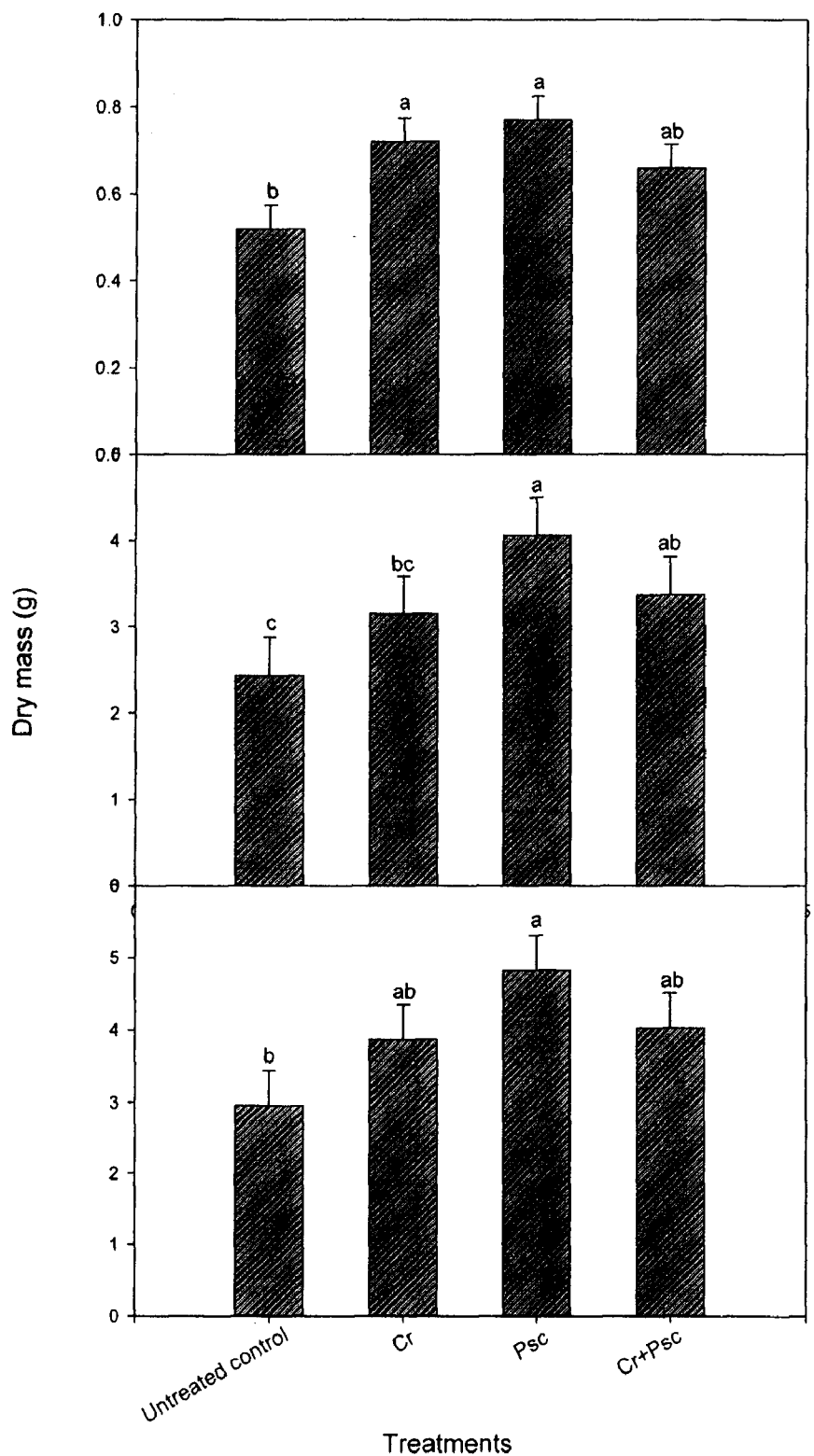
FIG. 3 shows the effects of *Clonostachys rosea* and *Pseudomonas chlorographis* on dry mass of roots, shoots and whole plants of hydroponic cucumbers.

FIGS. 2 and 3 demonstrate the active uptake of N, P, K nutrient solutions with C. rosea, strain as measured by leaf net $CO_2$ assimilation, leaf chlorophyll fluorescence, and plant growth in hydroponic cucumbers as measured by leaf area and dry mass differences.

EXAMPLE 16

Plants of cucumber (*Cucumis sativus* L.) 'Loustik' were grown from seeds in rockwool plugs (2.5 cm×2.5 cm×4.0 cm) and transferred to single-plant hydroponic units when 8-10 cm tall. In each unit, a plant was positioned with the plug in a hole in the centre of the lid of a 1.9 L white plastic container that was filled with nutrient solution (N:P:K, 20:8:20; pH 6.0; electrical conductivity 2.5 mS·cm$^{-1}$). The container was inserted into a black plastic pot, and the lid and plug were covered with black-on-white plastic sheeting, black side downwards. Compressed air with flow regulated by an aquarium air valve was bubbled continuously into the solution in each container to maintain the dissolved oxygen level near 8.6 mg/L. The plants were kept in a research greenhouse with air temperature near 25° C. during daytime (0800-1600 hours) and 22° C. at night. Temperature of the nutrient solution ranged from 22.0-23.6° C.

Inoculum of *C. rosea* and *Ps. chlororaphis* was applied separately and in combination to the nutrient solution to determine effects of the microbes on net $CO_2$ assimilation, leaf chlorophyll fluorescence, and plant growth. Final concentration of each microbe was 1×10$^5$ CFU mL$^{-1}$ nutrient solution. Untreated control plants received no inoculum.

EXAMPLE 17

Title: Greenhouse Soybean Inoculant Trial to show growth promotion with and without a nitrogen fixing *rhizobium* bacteria as a seed treatment.

TABLE 15

Figure 4:
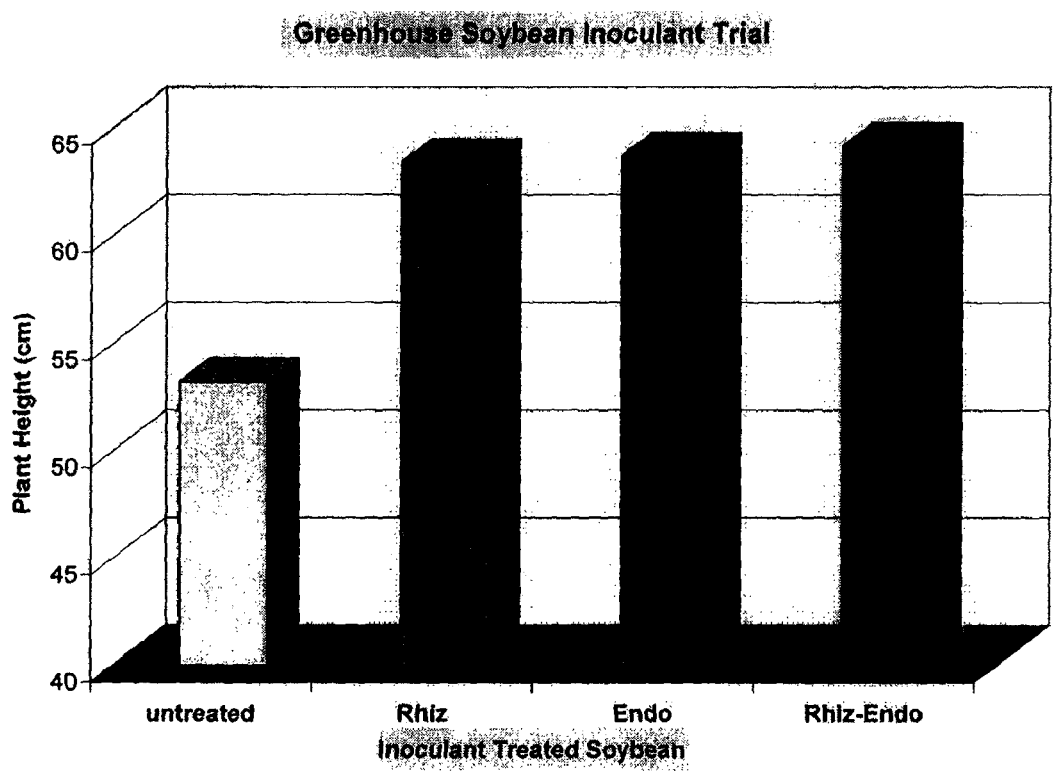
FIGS. 4-8 show the results of greenhouse soybean inoculant trials.

Variety: OAC Kent (Round-Up Ready)
EndoFine Seed treatment rate: 5 g/kg
Fertilizer treatment: 20-8-20 applied every 2 days at
25-100 g/100 L all treatments
*Rhizobium* seed treatment rate: 0.28 ml per 100 g of seed
Cell-Tech Nitrogen Inc A) Plant Height cm (multiple reps) (see FIG. 4)

| Treatment: | Average plant Height | % Difference over untreated |
|---|---|---|
| EndoFine | 63.74 | 19.5% |
| *Rhizobium* | 63.40 | 18.8% |
| EndoFine + *Rhizobium* | 64.18 | 20.3% |
| Untreated | 53.35 | na |

Figure 5:
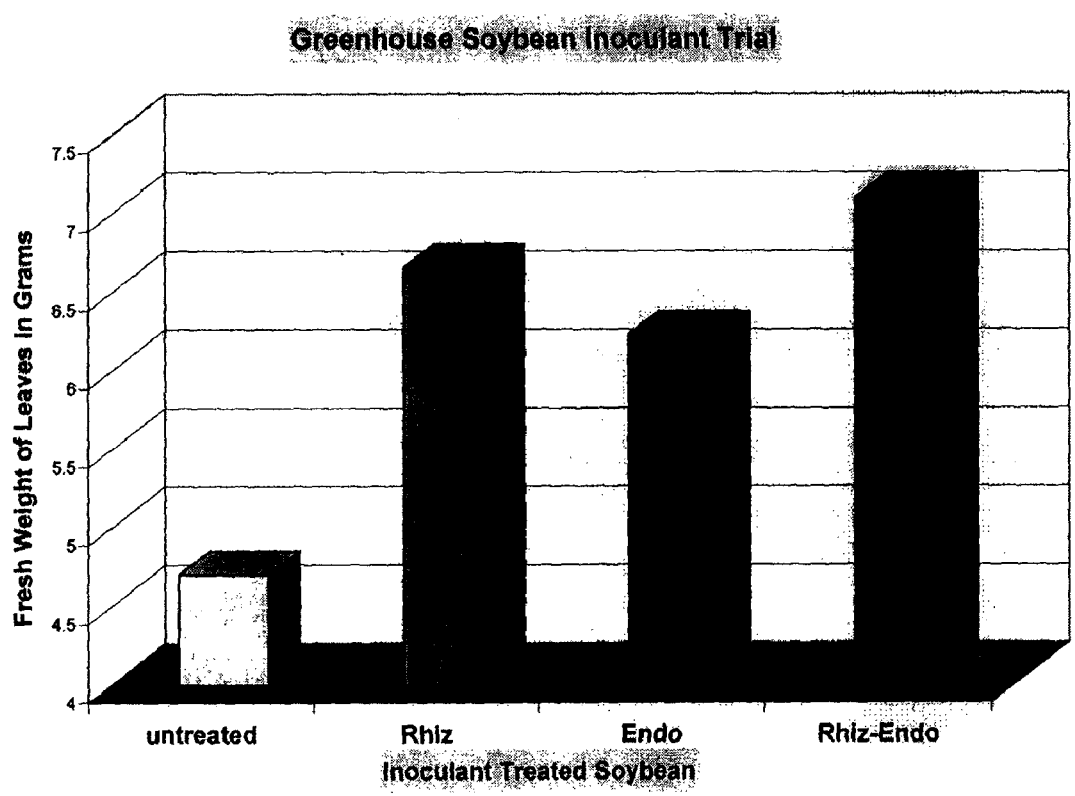

B) Plant Fresh weight leaves (multiple reps) (see FIG. 5)

| Treatment: | Average Fresh weight in grams | % Difference over untreated |
|---|---|---|
| EndoFine | 6.23 | 10.5% |
| *Rhizobium* | 6.66 | 18.1% |
| EndoFine + *Rhizobium* | 7.10 | 25.9% |
| Untreated | 5.64 | na |

Figure 6:
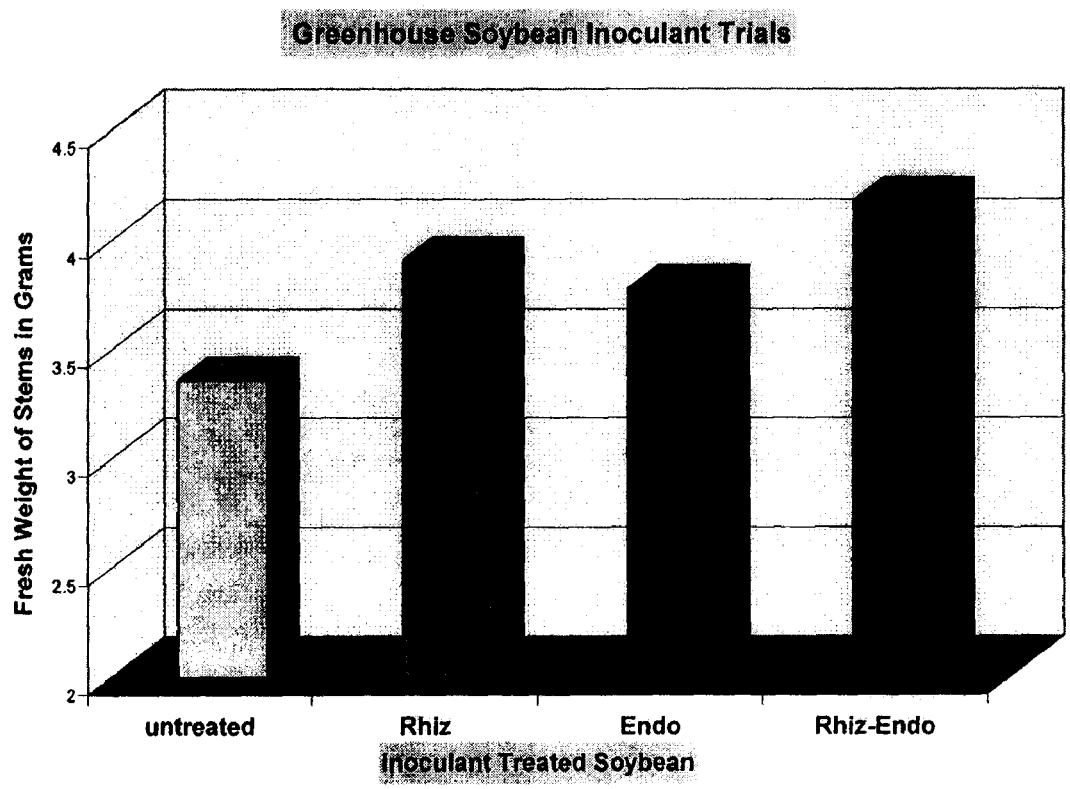

C) Plant Fresh weight stems (multiple reps) (see FIG. 6)

| Treatment: | Average Fresh weight in grams | % Difference over untreated |
|---|---|---|
| EndoFine | 3.776 | 20.6% |
| *Rhizobium* | 3.912 | 25.0% |
| EndoFine + *Rhizobium* | 4.184 | 33.7% |
| Untreated | 3.13 | na |

Figure 7:
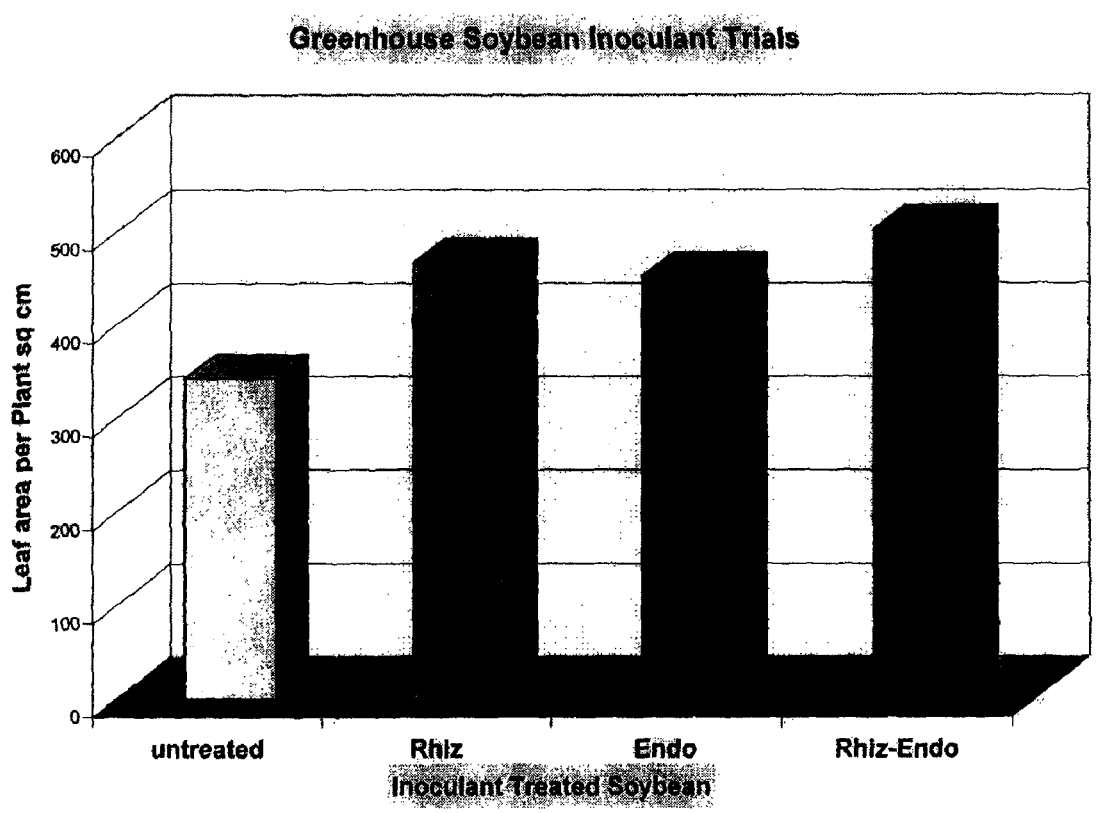

D) Plant Leaf Area (multiple reps) (see FIG. 7)

| Treatment: | Average Leaf Area per plant sq cm | % Difference over untreated |
|---|---|---|
| EndoFine | 452.22 | 16.0% |
| *Rhizobium* | 467.26 | 19.9% |
| EndoFine + *Rhizobium* | 502.54 | 28.9% |
| Untreated | 389.74 | na |

Figure 8:
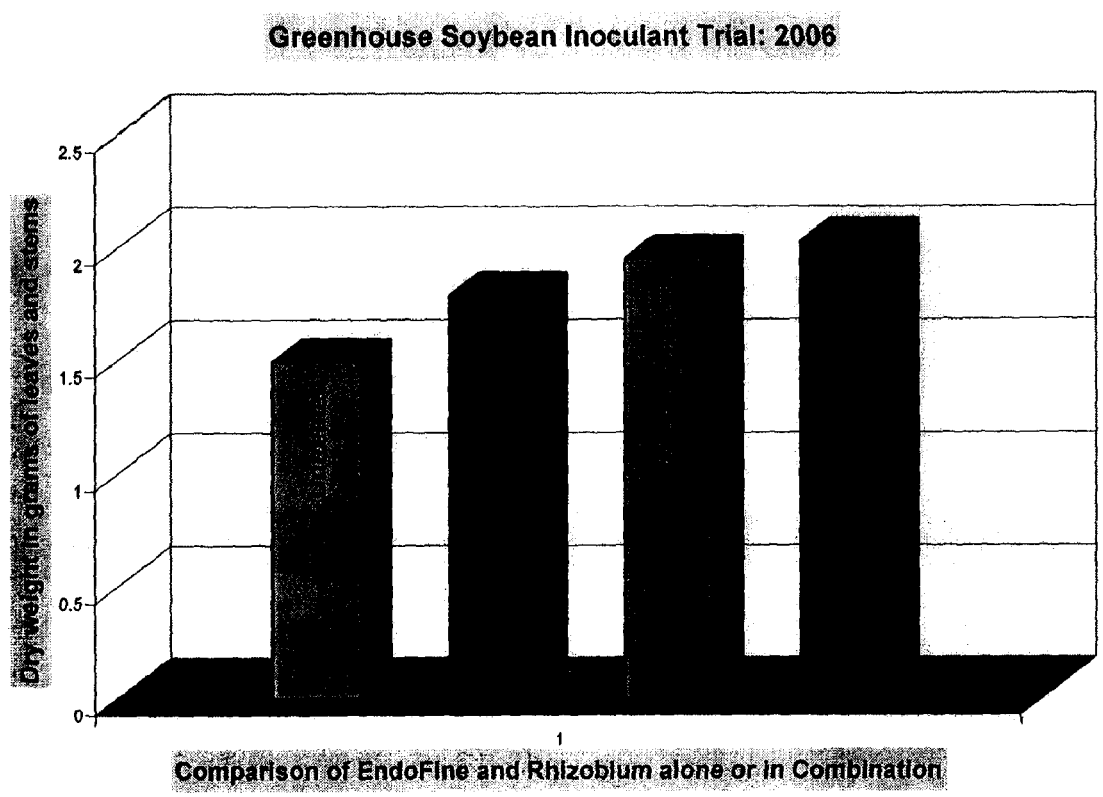

E) Plant dry weight leaves + stems (multiple reps) (see FIG. 8)

| Treatment: | Average Plant dry weight grams Leaf + stem | % Difference over untreated |
|---|---|---|
| EndoFine | 1.787 | 19.8% |
| *Rhizobium* | 1.948 | 30.6% |
| EndoFine + *Rhizobium* | 2.026 | 35.8% |
| Untreated | 1.492 | na |

The Endophyte *Clonostachys rosea*, Strain 88-710 Formulations that Provide Additional/Additive Plant Protection Benefits Against Plant Diseases, Insects and Mites

EXAMPLE 18

Tables 16. Examples A, B, C, D and F demonstrate the performance of *C. rosea* strain 88-710 on protection against powdery mildew(s), two spotted mites, and red aphids re use cucumber, roses in grower greenhouse trials.

TABLE 16

*Clonostachys rosea* strain 88-710 wound healing benefits as inoculant formulations for added value plant protective benefits against disease, insect and mites.

A) Cucumber Grower Trials (Greenhouse) for powdery mildew *Erysiphe cichoracearum*; *Erysiphe* spp,. *Sphaerotheca fuliginea*.) 5 replicates ADJ 702 applied at 16 g/L once to foliage

| Treatment: | Average % reduction of mycelium/spores Days after treatment | | |
|---|---|---|---|
| | 5 | 7 | 10 |
| ADJ 702 (formulation of *C. rosea*) | 99.7 | 99.7 | 99.0 |
| Untreated | 0 | 0 | 0 |
| Chemical Fungicide Programs (thiophanate methyl, myclobutanil, pyraclostrobin + boscalid)* | 90 | 70 | 50 |

*powdery mildew complex believed to be resistant to fungicide sprays; some injury to foliage
**ADJ 702 safety to cucumber foliage was excellent B) Trials on Roses (10 replicates in greenhouse grower) powdery mildew *Sphaerotheca pannosa* var. *rosea* ADJ 700 applied at 16 g/L to foliage

| Treatment: | Average % reduction of mycelium/spores Days after treatment | | |
|---|---|---|---|
| | 5 | 7 | 10 |
| ADJ 702 (formulation of *C. rosea*) | 98.0 | 99.5 | 99.0 |
| Untreated | 0 | 0 | 0 |
| Chemical Fungicide Programs (thiophanate Methyl, sulfur, dodomorph)* | 80 | 60 | 40 |

*powdery mildew fungicides believed to be resistant to powdery mildew and some foliage injury to rose plants/tender leaves from chemical treatments
**safety to rose foliage (all stages excellent)

C) Trails on roses for red aphid reductions (5 grower greenhouse trails) *Macrosyshum* spp., *Aphis* spp. *Myzaphis* spp. ADJ 702 32 g/L treatment twice (within 2 days) to foliage

| Treatment: | Average % reduction aphids/eggs) Days after treatment | | | |
|---|---|---|---|---|
| | 2 | 5 | 10 | 15 |
| ADJ 702 (two applications) (formulation of *C. rosea*) | 90 | 95 | 98 | 98 |
| Untreated | 0 | 0 | | 0 |
| Chemical insecticide Programs* | 50 | 40 | | 20 |

*aphids believed to be resistant and some foliage injury to rose plants
**plant safety for ADJ 702 applications excellent D) Residual effect on protection from powdery mildews, cucumbers greenhouse trials

| Treatment: | Average Disease (mycelium/spores) % control Days after treatment | | |
|---|---|---|---|
| | 5 | 7 | 10 |
| ADJ 702 (formulation of *C. rosea*) 16 g/L spray | 98.0 | 99.5 | 99.0 |
| Untreated | 0 | 0 | 0 |
| Chemical Fungicide Programs (thiophanate Methyl, sulfur, dodomorph) | 80 | 60 | 40 |

E) Grower trials on roses (greenhouse) for mite protection (two spotted mite, *Tetranychus urticae*) ADJ 702 16 g/L treatment twice (within 2 days) to foliage

| Treatment: | Average % reduction adult mites, crawlers/eggs) Days after treatment | | | |
|---|---|---|---|---|
| | 2 | 5 | 10 | 15 |
| ADJ 702 (two applications) (formulation of *C. rosea*) | 95 | 98 | 99 | 99 |
| Untreated | 0 | 0 | | 0 |
| Chemical insecticide Programs* | 50 | 70 | | 80 |

*mites believed to be resistant and some foliage injury to rose plants from chemical treatments
**plant safety for ADJ 702 applications excellent F) Grower trials on cucumbers (greenhouse) for mite protection (two spotted mite, *Tetranychus urticae*) ADJ 702 16 g/L treatment twice (within 2 days) sprays to foliage

| Treatment: | Average % reduction adult mites, crawlers/eggs) Days after treatment | | | |
|---|---|---|---|---|
| | 2 | 5 | 10 | 15 |
| ADJ 702 (two applications) (formulation of *C. rosea*) | 98 | 98 | 99 | 99 |
| Untreated | 0 | 0 | | 0 |
| Chemical insecticide Programs* | 70 | 70 | | 80 |

*mites believed to be resistant treatments
**plant safety for ADJ 702 applications excellent The Endophyte *Clonostachys rosea*, Strain 88-710 can be Combined with Rooting Hormones to Provide Added Value Rooting Benefits to Cuttings/Transplants/Grafting of Plant Tissue.

EXAMPLE 19

FIGS. 9 and 10 demonstrate that *Clonostachys rosea*, strain 88-710 can be used in combination with rooting hormone products such as IBA (indole-3-butyric acid) for the benefit of rooting and inoculant benefits i.e. *C. rosea* colonization and plant growth. FIG. 9 shows colonisation of rose plant shoots and roots using EndoFine alone and in combination with IBA rooting compound. FIG. 10 shows Root weight Gains of rose plant roots and roots using EndoFine alone and in combination with IBA rooting compound.

EXAMPLE 20

ENDOFINE concentrate as a dry seed treatment for enhancement of seed germination and plant growth (growth room trials).

TABLE 17

Soybean: Variety AC Kent;
4 replicates × 7 treatments × 4 samplings = 112 plants Microbial agent and application
E-D = Endofine ® dry powder 3.7 × 10⁸ CFU/g @
5 g/Kg of seed as a coating (4.7 × 10 spores/seed)
Fertilizer treatment: 20-8-20 applied every 2 days at 25-100 g/100 L all treatments Seed treatment with Endofine ™ on emergence and roots weight of soybean

| | | | Weight of Roots (g) | | | | | |
|---|---|---|---|---|---|---|---|---|
| | | % Diff. Over | | | | % Average diff. Over untreated | | |
| Treatment | Emergence (%) | untreated | 10 days | 20 days | 30 days | 10 | 20 | 30 days |
| CK1* | (untreated) 55 | na | 3.52 | 4.23 | 5.76 | | na | |
| E-D* | (EndoFine) 95 | 72.7 | 4.28 | 4.60 | 6.96 | 21.5 | 8.7 | 20.8 |

Density of CFU of *C. rosea* recovered from the rhizosphere of the seed treated soybean in Mix-potre soil in growth room

| | | CFU/1000 Colonisation days after | | |
|---|---|---|---|---|
| Plant part | Colonisation of seed | 10 | 20 | 30 |
| E-D-P (EndoFine primary roots) | 4.67 × 10 to the fourth spores per seed | 88 | 12 | 160 |
| E-D-S (EndoFine secondary roots) | | 70.5 | 1 | 10 |
| E-D-F (EndoFine fibrous roots) | | 0 | 2 | 25 |
| Untreated | 0 | 0 | 0 | 0 |

EXAMPLE 21

The Genetic Identification of *Clonostachys rosea* Strain 88-710

Sampling of soils from 18 different locations in Ontario has indicated that the 18S rRNA gene sequence of the strain 88-710 with "GeneBank", has found that the 18S sequence of the 88-710 strain does not have intron sequence that *Bionectria ochroleuca* has (See Definitions). This indicates that the *Clonostachys* strain 88-710 does not belong to *Bionectria ochroleuca*. However the strain 88-710 is 100% homologous to *C. rosea* based on a comparison of internal transcribed spacer (ITS) and the 28S rRNA gene sequences "GeneBank". Hence the strain *Clonostachys* strain 88-710 does not produce the sexual state (teleomorph) and is genetically unique.

REFERENCES

| U.S. PAT. | DATE | INVENTOR(S) |
|---|---|---|
| 6,911,338 | Jun. 28, 2005 | Strobel et al |
| 6,815,591 | Nov. 9, 2004 | Hignight et al |
| 6,495,113 | Dec. 17, 2002 | Xue |
| 6,475,566 | Nov. 5, 2002 | Messner et al |
| 6,306,390 | Oct. 23, 2001 | Narisawa |
| 5,723,720 | Mar. 3, 1998 | Brede at al |
| 5,534,252 | Jul. 9, 1996 | McAfee et al |
| 5,407,826 | Apr. 18, 1995 | Matsuoka et al |
| 5,068,105 | Nov. 26, 1991 | Lewis et al |
| 4,550,527 | Nov. 5, 1985 | Hall et al |
| 4,294,037 | Oct. 13, 1881 | Mosse et al |

US Patent application 20050063955, Mar. 24, 2005; Elmer, Philip Albert George et al Other References
1. Domsch, K. H., W. and Anderson. T.-H. 1980 Compendium of Soil Fungi. Academic Press, London
2. Pugh, G. J. F., and Dickinson, C. H. 1965. Studies on fungi in coastal soils, VI, *Gliocladium roseum* Bainier. Trans. Br. Mycol, Soc. 48:279-285

The invention claimed is:

1. A method of stimulating and providing an additive effect with *rhizobium* on production of nitrogen fixing nodules on legumes and to enhance plant growth, which method comprises applying a stabilized endophyte inoculant composition comprising a vegetative or conidial phase of *Clonostachys rosea* in admixture with an agrochemically acceptable stabilizer carrier to said legumes.

2. The method of claim 1 wherein the agrochemically acceptable stabilizer carrier comprises an emulsifier.

3. The method of claim 2 wherein the emulsifier is biologically derived.

4. The method of claim 3 wherein the emulsifier is cereal grain or an extract or flour thereof.

5. The method of claim 1 wherein the stabilized endophyte inoculant composition is in water-based sprayable form.

6. The method of claim 1 wherein the stabilized endophyte inoculant composition is in the form of a dust.

7. The method of claim 1 wherein the stabilized endophyte inoculant composition comprises the vegetative or conidial phase of *Clonostachys rosea* strain 88-710.

8. The method of claim 1 wherein the stabilized endophyte inoculant composition has a pH of 6 to 8.

9. The method of claim 1 wherein the stabilized endophyte inoculant composition comprises 106 to 1012 spores/gram of said composition.

10. The method of claim 1 wherein the stabilized endophyte inoculant composition comprises 107 to 1010 spores/gram of said composition.

11. The method of claim 1 wherein the *Clonostachys rosea*, strain 88-710 is unique in terms of genetic profile and is an endophyte wherein the strain does not produce the sexual state (teleomorph) as does the anamorph referred to as *Bionectria ochroleuca* which is morphologically indistinguishable from *Clonostachys rosea*.

12. A method of providing inoculant or rooting benefits to a cutting or plant transplant, which method comprises applying a stabilized endophyte inoculant composition comprising a vegetative or conidial phase of *Clonostachys rosea* in admixture with an agrochemically acceptable stabilizer carrier with a rooting hormone to said cutting or plant transplant.

13. The method of claim 12 wherein said rooting hormone is indole-3-butyric acid (IBA).

14. A method of providing inoculant or rooting benefits to a cutting or plant transplant with robotic equipment using formulations that do not interrupt robotic sensing equipment by leaving sensor sensitive dust particles on plant material during transplanting, which method comprises applying a stabilized endophyte inoculant composition comprising a vegetative or conidial phase of *Clonostachys rosea* in admixture with an agrochemically acceptable stabilizer carrier with a rooting hormone to said cutting or plant transplant.

15. The method of claim 14 wherein said rooting hormone is indole-3-butyric acid (IBA).

* * * * *